(12) United States Patent
Rivera et al.

(10) Patent No.: US 10,352,856 B2
(45) Date of Patent: Jul. 16, 2019

(54) APPARATUS AND METHODS FOR SPECTROSCOPY AND BROADBAND LIGHT EMISSION USING TWO-DIMENSIONAL PLASMON FIELDS

(71) Applicant: Massachusetts Institute of Technology, Cambridge, MA (US)

(72) Inventors: Nicholas Rivera, Cambridge, MA (US); Ido Kaminer, Cambridge, MA (US); Bo Zhen, Boston, MA (US); Marin Soljacic, Belmont, MA (US); John Joannopoulos, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/378,782

(22) Filed: Dec. 14, 2016

(65) Prior Publication Data
US 2017/0167977 A1    Jun. 15, 2017

Related U.S. Application Data

(60) Provisional application No. 62/266,762, filed on Dec. 14, 2015, provisional application No. 62/342,287, filed on May 27, 2016.

(51) Int. Cl.
   *G01N 21/64* (2006.01)
   *G01N 21/63* (2006.01)
   *G01N 21/17* (2006.01)

(52) U.S. Cl.
   CPC .......... *G01N 21/64* (2013.01); *G01N 21/636* (2013.01); *G01N 2021/1725* (2013.01)

(58) Field of Classification Search
   CPC ................. G01N 21/64; G01N 21/636; G01N 2021/1725; G01N 21/658;
   (Continued)

(56) References Cited

U.S. PATENT DOCUMENTS 6,897,436 B2    5/2005    Smolyaninov et al.
6,985,223 B2    1/2006    Drachev et al.
(Continued)

OTHER PUBLICATIONS https://phys.org/news/2012-09-topographical-approaches-graphene-thickness.html.*
(Continued)

*Primary Examiner* — Mohamed K Amara
(74) *Attorney, Agent, or Firm* — Smith Baluch LLP

(57) ABSTRACT

Ultra-thin conductors are employed to generate plasmon fields near the surface of the conductors. Emitters, such as atoms, molecules, quantum dots, or quantum wells, in the plasmon fields can emit and absorb light via transitions that are otherwise forbidden in the absence of the plasmon fields. Applications using these forbidden transitions include spectroscopy, organic light sources, and broadband light generation. For example, in a spectroscopic platform, an emitter is disposed in the plasmon fields to excite electronic transitions that are otherwise unexcitable. In organic light sources, plasmon fields quench excited triplet states, allowing fast singlet decay with the emission of light. In broadband light generation, strong two-plasmon spontaneous emission of emitters near ultrathin conductors is employed to produce a broad spectrum of light.

15 Claims, 25 Drawing Sheets

(58) Field of Classification Search
CPC ........... G01N 33/48721; G01N 27/028; G01N 2021/651; G01J 3/0267; G01J 3/44; C12Q 1/6869; B82Y 5/00; B82Y 15/00; B82Y 30/00; B82Y 40/00; B21D 22/00; H04N 21/2146; H04N 21/4784; H04N 21/422; H04N 7/18; H04N 21/812; H04N 21/4126; B64D 11/0015; G03F 7/00; C23C 16/26; C23C 14/18; C23C 16/0227; C23C 16/01; C23C 14/30; G01L 1/18
See application file for complete search history.

(56) References Cited

U.S. PATENT DOCUMENTS

| | | | | |
|---|---|---|---|---|
| 7,351,588 | B2 | 4/2008 | Poponin | |
| 7,760,364 | B1* | 7/2010 | Zhuang | B82Y 20/00 356/237.1 |
| 8,395,774 | B2 | 3/2013 | Afzali et al. | |
| 8,699,032 | B2 | 4/2014 | Nakatani et al. | |
| 8,766,181 | B2* | 7/2014 | Zewail | H01J 37/26 250/306 |
| 9,423,345 | B2* | 8/2016 | Avouris | G01N 21/554 |
| 9,470,632 | B2* | 10/2016 | Farmer | G01N 21/553 |
| 9,594,262 | B2* | 3/2017 | Zheludev | G02F 1/0126 |
| 9,645,291 | B1* | 5/2017 | Sommer | G02B 5/204 |
| 9,678,012 | B2* | 6/2017 | Rothberg | C12Q 1/6874 |
| 9,921,157 | B2* | 3/2018 | Rothberg | G01N 21/6408 |
| 9,927,675 | B2* | 3/2018 | Huang | H01L 31/00 |
| 2010/0291828 | A1* | 11/2010 | Reches | A61L 27/38 442/340 |
| 2011/0285999 | A1* | 11/2011 | Kim | G01N 21/552 356/445 |
| 2012/0134880 | A1* | 5/2012 | Kurkina | G01N 27/4146 422/82.01 |
| 2013/0010300 | A1 | 1/2013 | Tamura et al. | |
| 2015/0141267 | A1* | 5/2015 | Rothberg | C12Q 1/6869 506/2 |
| 2015/0293025 | A1* | 10/2015 | Ninomiya | C23C 14/58 356/244 |
| 2017/0088944 | A1* | 3/2017 | Sultana | C23C 16/26 |
| 2017/0146456 | A1* | 5/2017 | Li | C07F 7/1804 |
| 2017/0299784 | A1* | 10/2017 | Mikkelsen | H01L 33/26 |
| 2018/0052186 | A1* | 2/2018 | Su | G01N 21/35 |
| 2018/0372777 | A1* | 12/2018 | De Louren O E Vasconcelos | G01R 1/067 |

OTHER PUBLICATIONS

"Fabrication of quantum-dot devices in graphene", Moriyama et al. STAM, 11 (2010) pp. 1-5.*

Atwater, "The promise of plasmonics," Scientific American, 296(4):56-62, Apr. 2007.

Caldwell et al., "Low-loss, infrared and terahertz nanophotonics using surface phonon polaritons," Nanophotonics, 4(1), pp. 44-68, Jul. 19, 2014.

Caldwell et al., "Low-loss, extreme subdiffraction photon confinement via silicon carbide localized surface phonon polariton resonators," Nano letters, 13(8):3690-3697, 2013.

Caldwell et al., "Mid-infrared nanophotonics," Nature materials, 14(4):364-366, Apr. 2015.

Caldwell et al., "Sub-diffractional volume-confined polaritons in the natural hyperbolic material hexagonal boron nitride," Nature communications, 5, 41 pages, Aug. 2014.

Dai et al., "Graphene on hexagonal boron nitride as a tunable hyperbolic metamaterial," Nature nanotechnology, 10(8):682-686, Jun. 22, 2015.

Dai et al., "Subdiffractional focusing and guiding of polaritonic rays in a natural hyperbolic material," Nature communications, 6:6963, 7 pages, Apr. 22, 2015.

Dai et al., "Tunable phonon polaritons in atomically thin van der waals crystals of boron nitride," Science, 343(6175):1125-1129, Mar. 7, 2014.

Diaconescu et al., "Low-energy acoustic plasmons at metal surfaces," Nature, Letters, vol. 448(7149), pp. 57-59, Jul. 2007.

Fei et al., "Infrared nanoscopy of dirac plasmons at the graphene-sio2 interface," Nano letters. 11(11):4701-4705, 2011.

Fei et al., "Gate-tuning of graphene plasmons revealed by infrared nano-imaging," Nature, 487(7405):82-85, Jul. 5, 2012.

Feng et al., "Localized surface phonon polariton resonances in polar gallium nitride," Applied Physics Letters, 107(8):081108, Aug. 24, 2015.

Grigorenko et al., "Graphene plasmonics," Nature photonics, 6(11):749-758, Oct. 31, 2012.

Hayat et al., "Measurement and model of the infrared two-photon emission spectrum of gaAs," Physical review letters, 103(2):023601, Jul. 10, 2009.

Hayat et al., "Observation of two-photon emission from semiconductors," Nature photonics, 2(4):238-241, Apr. 2008.

Hillenbrand et al., "Phonon-enhanced light-matter interaction at the nanometre scale," Nature, 418(6894):159-162, Jul. 11, 2002.

Jablan et al., "Plasmonics in graphene at infrared frequencies," The American Physical Society, Physical Review B, 80(24):245435, Dec. 23, 2009.

Kauranen et al., "Nonlinear plasmonics," Nature Photonics, 6(11):737-748, Oct. 31, 2012.

Khurgin "How to deal with the loss in plasmonics and metamaterials," Nature nanotechnology, 10(1):2-6, Jan. 2015.

Knöll et al., "Qed in dispersing and absorbing media," from *Coherence and Statistics of Photons and Atoms*, edited by J. Perina (Wiley, New York, 2001), 60 pages.

Koppens et al., "Graphene plasmonics: a platform for strong light-matter interactions," Nano letters, 11(8):3370-3377, 2011.

Kumar et al., "Tunable light-matter interaction and the role of hyperbolicity in graphene-hbn system," Nano letters, 15(5):3172-3180, Apr. 21, 2015.

Li et al., "Hyperbolic phonon-polaritons in boron nitride for near-field optical imaging and focusing," Nature communications, 6:7507, 9 pages, Jun. 26, 2015.

Liu et al., "Plasmon dispersion and damping in electrically isolated two-dimensional charge sheets," The American Physical Society, Physical Review B, 78(20):201403, Nov. 5, 2008.

Low et al., "Graphene plasmonics for terahertz to mid-infrared applications," Acs Nano, 8(2):1086-1101, 2014.

Moskovits, "Surface-enhanced raman spectroscopy: a brief retrospective," Journal of Raman Spectroscopy, 36(6-7):485-196, 2005.

Moskovits, "Surface-enhanced spectroscopy," Reviews of modern physics, 57(3):783, Jul. 1985.

Muñoz et al., "Emitters of n-photon bundles," Nature photonics, 8(7):550-555, Jun. 1, 2014.

Nagao et al., "Dispersion and damping of a two-dimensional plasmon in a metallic surface-state band," Physical review letters, 86(25):5747, Jun. 18, 2001.

Nevet et al., Plasmonic nanoantennas for broad-band enhancement of two-photon emission from semi-conductors, Nano letters, 10(5):1848-1852, 2010.

Ota et al, "Spontaneous two-photon emission from a single quantum dot," Physical review letters, 107(23):233602, Dec. 2, 2011.

Park et al., "Acoustic plasmon on the au(111) surface," The American Physical Society, Physical Review Letters, 105:016801, Jul. 1, 2010.

Pelton, "Modified spontaneous emission in nanophotonic structures," Nature Photonics, 9(7):427-435, Jun. 30, 2015.

Pietro et al., "Observation of dirac plasmons in a topological insulator," Nature Nanotechnology, vol. 8(8):556-560, Jul. 21, 2013.

Rivera et al., "2d plasmonics for enabling novel light-matter interactions," Science 353.6296 (2016): 263-269, arXiv: 1512.04598, Dec. 16, 2015.

Rubinowicz, "Multiple radiation in atomic spectra," Reports on progress in physics, 12(1):233, 1949.

Rugeramigabo et al., "Experimental investigation of two-dimensional plasmons in a $dysi_2$ monolayer on si (111)," The American Physical Society, Physical Review B, 78(15):155402, Oct. 1, 2008.

(56) References Cited

OTHER PUBLICATIONS

Tadaaki et al. "Dispersion and damping of a two-dimensional plasmon in a metallic surface state band," The American Physical Society, Physical review letters, vol. 86(25), pp. 5747-5750, Jun. 18, 2001.

Tame et al., "Quantum plasmonics," Nature Physics, 9(6)329-340, Jun. 3, 2013.

Tielrooij et al., "Electrical control of optical emitter relaxation pathways enabled by graphene," Nature Physics, vol. 11, 7 pages, Mar. 2015.

Tomadin et al., "Accessing phonon polaritons in hyperbolic crystals by angle-resolved photoemission spectroscopy," Physical review letters, 115(8):087401, Aug. 21, 2015.

Woessner et al., "Highly confined low-loss plasmons in graphene-boron nitride heterostructures," Nature materials, vol. 14, 5 pages, Dec. 22, 2014.

Xu et al., "Mid-infrared polaritonic coupling between boron nitride nanotubes and graphene," ACS nano, 8(11):11305-11312, 2014.

Yan et al., "Damping pathways of mid-infrared plasmons in graphene nanostructures," Nature Photonics, 7(5):394-399, May 2013.

Yoxall et al., "Direct observation of ultraslow hyperbolic polariton propagation with negative phase velocity," Nature Photonics, vol. 9, 6 pages, Sep. 14, 2015.

Zhang et al., "Graphene surface plasmons at the near-infrared optical regime," Scientific reports, 4:6559, 6 pages, Oct. 9, 2014.

International Search Report and Written Opinion dated Oct. 6, 2017 from International Application No. PCT/US16/66530, 18 pages.

\* cited by examiner

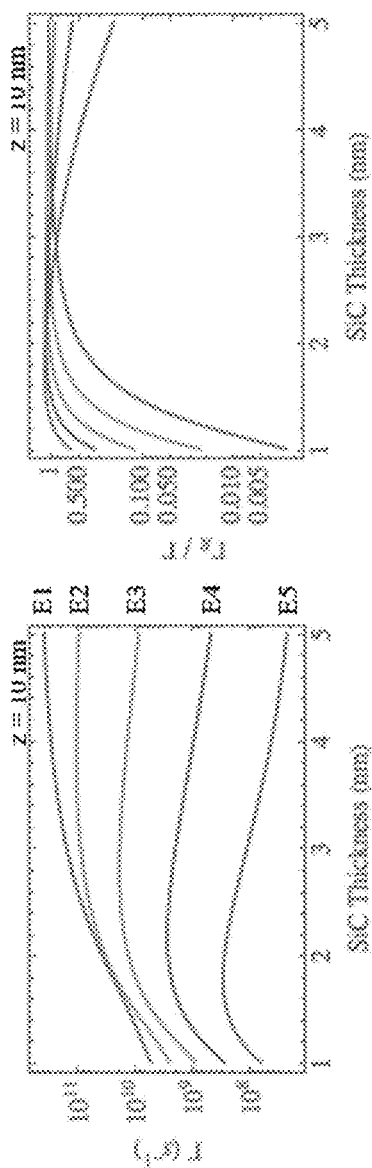
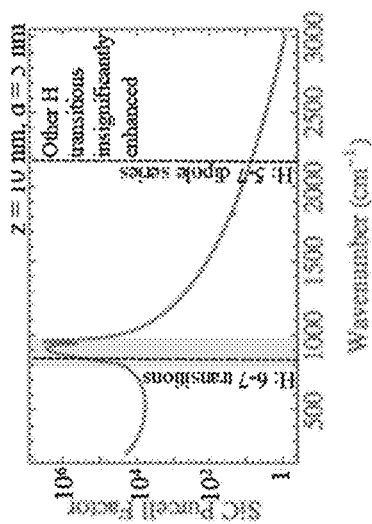
FIG. 14F
FIG. 14E
FIG. 14D

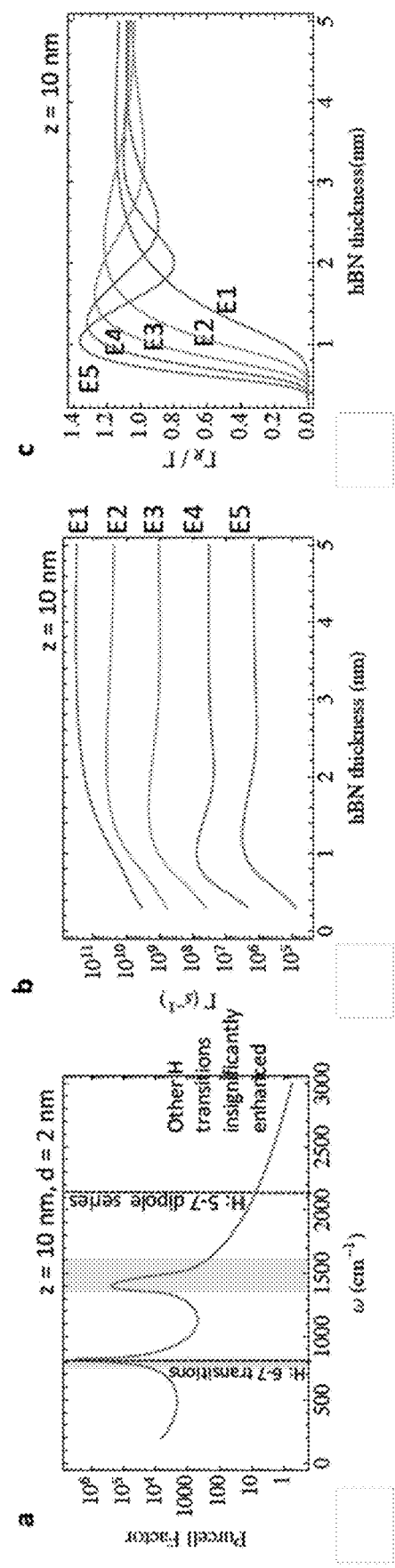

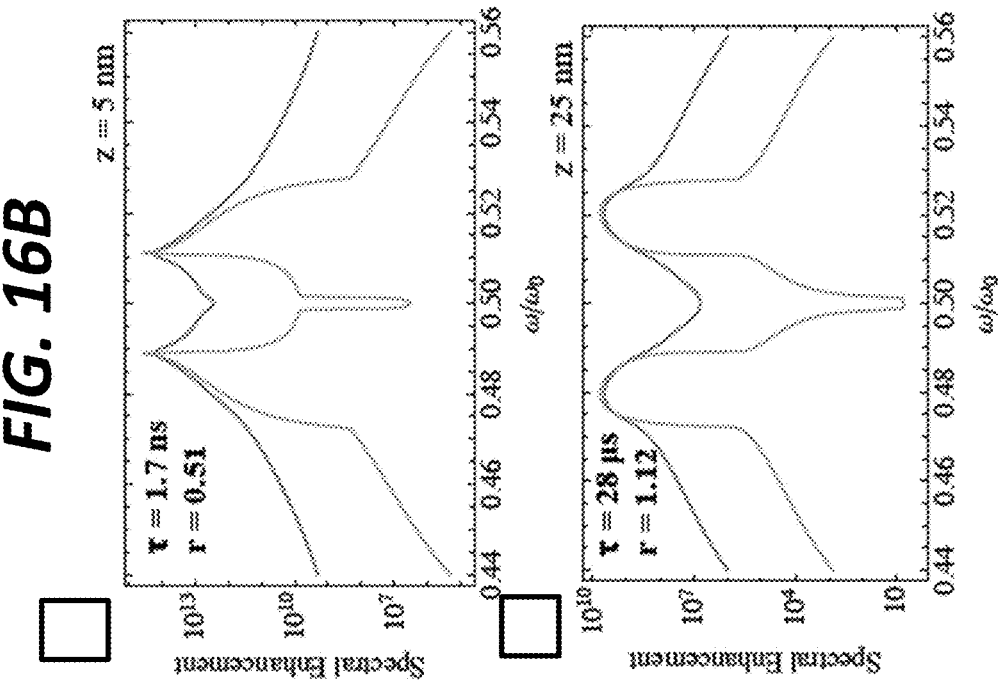
FIG. 16B
FIG. 16A
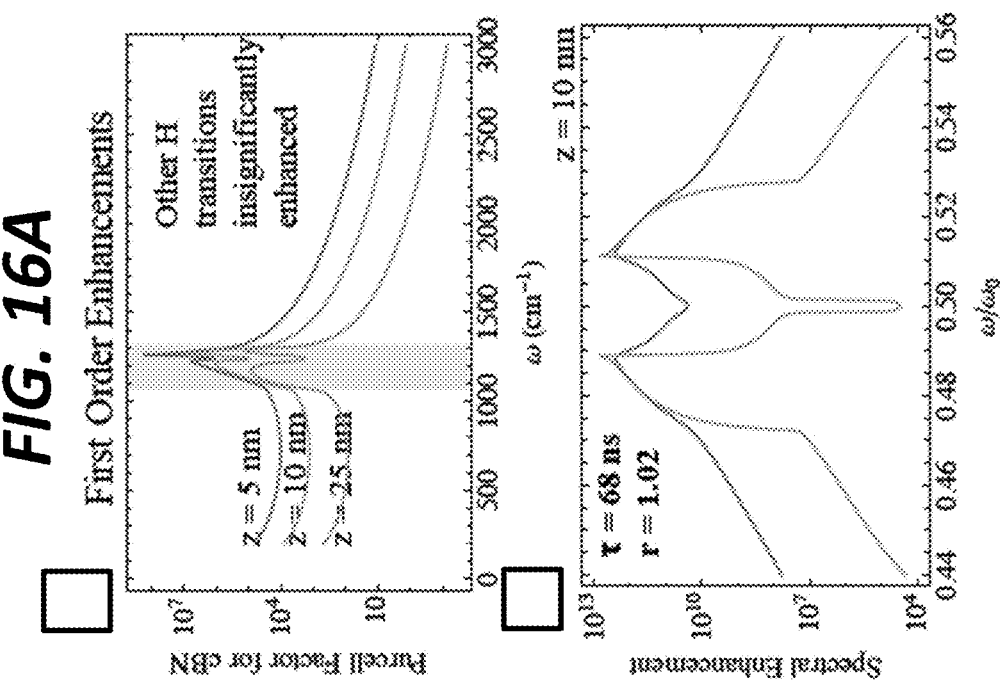
FIG. 16D
FIG. 16C

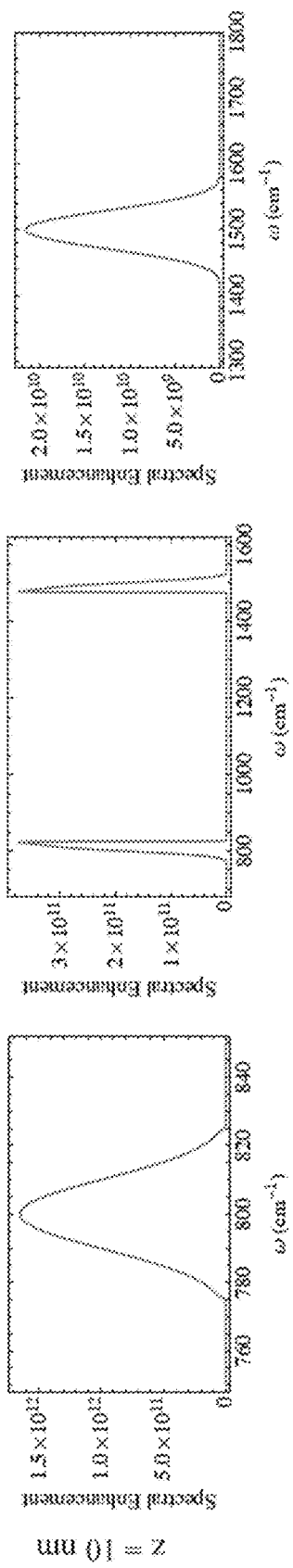

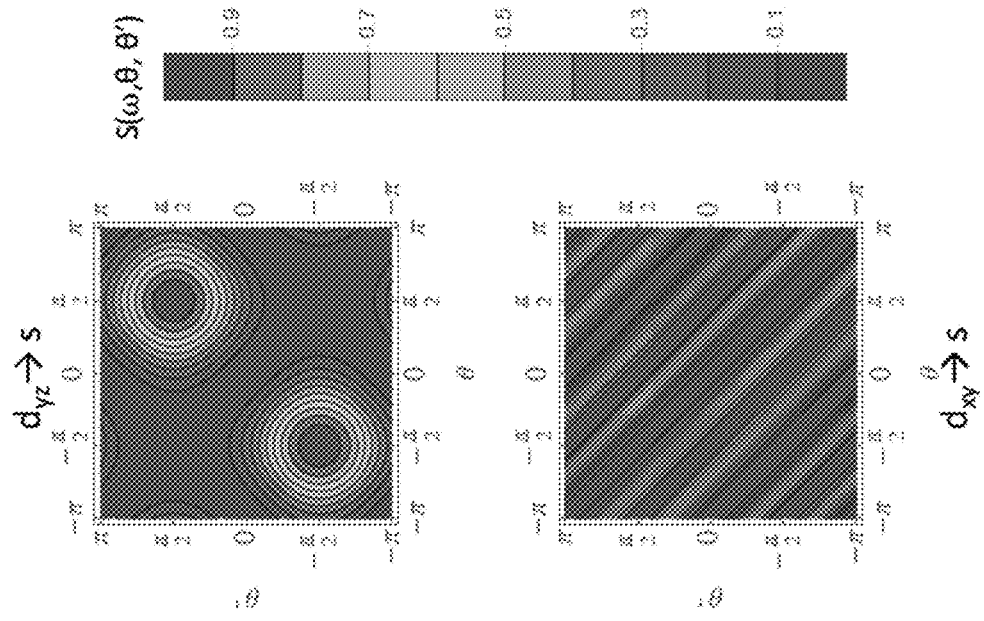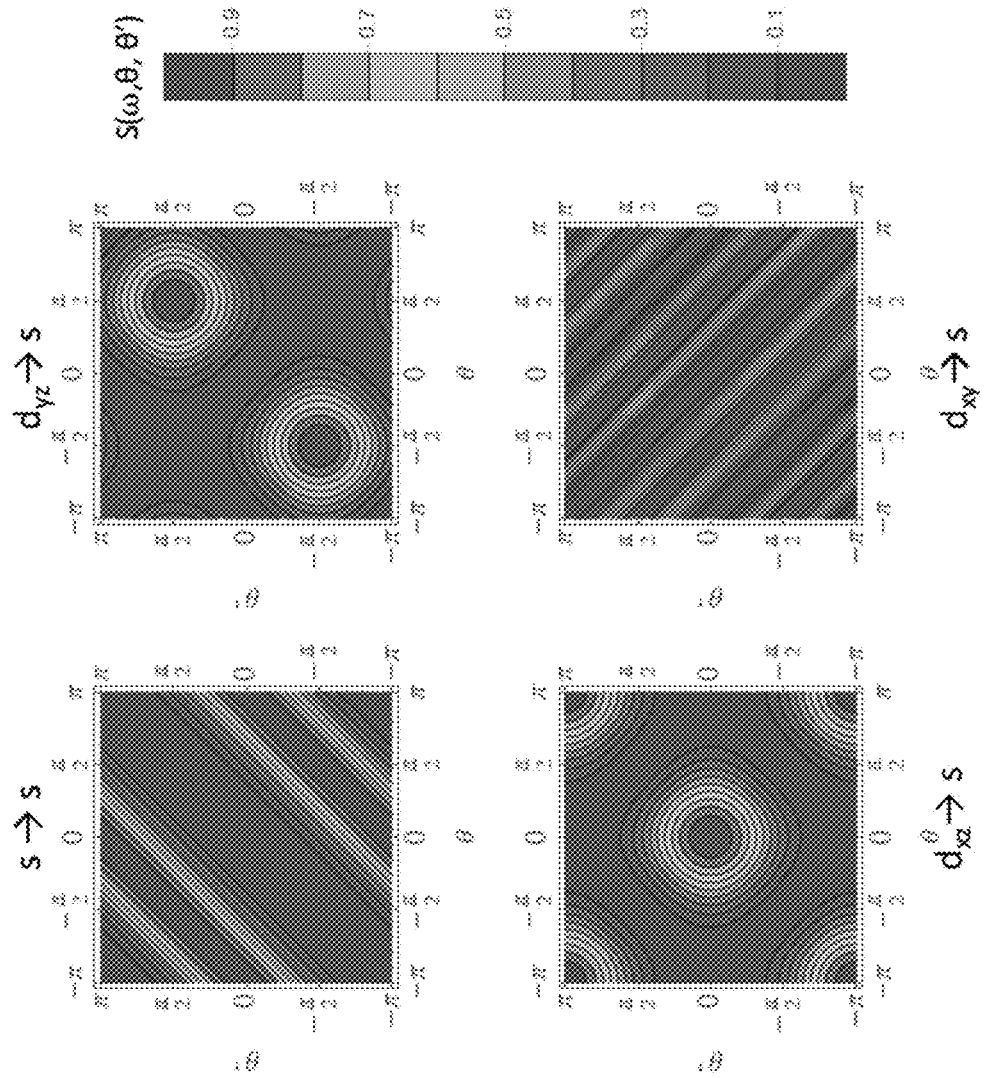
FIG. 18A
FIG. 18B
FIG. 18C
FIG. 18D

APPARATUS AND METHODS FOR SPECTROSCOPY AND BROADBAND LIGHT EMISSION USING TWO-DIMENSIONAL PLASMON FIELDS

CROSS-REFERENCES TO RELATED APPLICATIONS

This application claims priority to U.S. Application No. 62/266,762, filed Dec. 14, 2015, entitled "PLASMONS FOR SPECTROSCOPIC, LIGHT EMISSION, AND BROADBAND LIGHT GENERATION APPLICATIONS" and U.S. Application No. 62/342,287, filed May 27, 2016, entitled "METHODS AND APPARATUS FOR SPECTROSCOPIC LIGHT EMISSION AND BROADBAND LIGHT GENERATION," each of which is hereby incorporated herein by reference in their entirety for all purposes.

GOVERNMENT SUPPORT

This invention was made with Government support under Contract No. W911NF-13-D-0001 awarded by the Army Research Office. The Government has certain rights in the invention.

BACKGROUND

When an electron in an emitter (e.g., an atom or a molecule) is excited, the electron can relax by emitting light through various transition processes. These processes include, for example, multipolar process in which the orbital angular momentum of the electron changes by more than one, multiphoton process involving emission of two or more photons upon each transition, and spin-flip transitions where the electronic spin is flipped. Having access to these transition processes can benefit a wide range of technological areas.

For example, access to multipolar transitions can yield data on the electronic structure of atoms, molecules, and condensed matter by spectroscopic means. Moreover, access to multipolar transitions can also determine many electronic transitions within a short period time, thereby paving the way for single-shot spectroscopy.

In another example, having access to spin-flip transitions such as the singlet-triplet transition can be beneficial not only for spectroscopic applications, but also for quenching of organic molecules, which are often used in organic light sources. For example, in organic-dye lasers, a persistent challenge is that the population of excited electrons usually rapidly fills a triplet state. Because the singlet-triplet transition is slow, the electrons can remain in the triplet state for a long time. Increasing the population in the triplet state can accordingly decrease the population in the singlet state for lasing transitions. A high population of triplet states can also increase the lasing photon absorption and the number of molecules that are permanently lost through photobleaching, thereby limiting the lasing efficiency. Quenching of triplet states can reduce the population in triplet states, thereby increasing the lasing efficiency.

In yet another example, two-photon spontaneous emission processes can be used to construct broadband light sources. For example, a fast two-photon emitter can be used to turn a monochromatic beam of light into a broadband beam of light.

However, one common challenge to utilize the above mentioned transition processes is that these processes are usually too slow to be observable. The slow emission, without being bound by any particular theory or mode of operation, can be attributed to the long wavelength of the emitted light compared to the size of the emitter. Typically, the wavelength of light is about 1000 times to about 5000 times larger than the size of an atom. Currently, accessing the large set of extremely slow light emission processes remains a challenging technological problem.

SUMMARY

Embodiments of the present invention include apparatus, systems, and methods for spectroscopy and broadband light generation based on enhanced access to slow and forbidden transitions. In one example, an apparatus includes a conductive layer having a thickness less than 5 nm and a radiation source, in radiative communication with the conductive layer, to emit an excitation beam into the conductive layer. The excitation beam generates a two-dimensional (2D) plasmon field near a surface of the conductive layer. The apparatus also includes a light source, in optical communication with the conductive layer, to illuminate a sample in the 2D plasmon field with a probe beam. The sample absorbs at least one spectral component of the probe beam. The apparatus further includes a detector, in optical communication with the light source, to detect absorption of the at least one spectral component by the sample.

In another example, a method includes generating a two-dimensional (2D) plasmon field near a surface of a conductive layer having a thickness less than 5 nm and disposing a sample within the 2D plasmon field. The method also includes illuminating the 2D plasmon field with a probe beam, which causes the sample to absorb at least one spectral component in the probe beam, and detecting the absorption of the at least one spectral component.

In yet another example, an apparatus includes a conductive layer having a thickness less than 5 nm and at least one emitter disposed at a distance less than 10 nm away from a surface of the conductive layer. The apparatus also includes a light source, in optical communication with the conductive layer and the emitter, to illuminate the emitter with a monochromatic light beam at a wavelength selected to excite the emitter from a first energy state to a second energy state. The emitter relaxes to the first energy state by emitting at least two plasmons.

In yet another example, a method includes irradiating, with a monochromatic light beam, at least one emitter disposed at a distance less than 10 nm away from a surface of a conductive layer having a thickness less than 5 nm. The monochromatic light beam excites the emitter from a first energy state to a second energy state, and the emitter relaxes to the first energy state by emitting at least two plasmons.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 14A-14F show calculation results of multipolar transitions in a system using hBN and SiC layers having a thickness of 10 nm to generate phonon-polariton fields.

FIGS. 15A-15F show calculation results of multipolar transitions in a system using hBN and SiC layers having a thickness of 2 nm to generate phonon-polariton fields.

FIG. 16A shows Purcell spectra for a z-polarized dipole above 10 nm thick cBN at atom-surface separations of 5 nm, 10 nm, and 25 nm.

FIGS. 16B-16D show two-photon Purcell spectra for an s→s transition as a function of photon frequency ω for an emitter above a 10 nm thick cBN with atom-surface separations of 5 nm, 10 nm, and 25 nm, respectively.

FIGS. 17A-17I show two-polariton Purcell spectral enhancement for a spherical emitter as a function of emitter frequency at different distances away from an hBN surface.

FIGS. 18A-18D show plots of the angular spectra of two-photon emission with the initial state at s, $d_{xy}$, $d_{xz}$, and $d_{yz}$, respectively.

DETAILED DESCRIPTION

To gain access to the various slow emission processes, apparatus and methods described herein use light fields that are strongly confined to the surface of ultrathin conductors. These light fields are usually referred to as two-dimensional (2D) plasmon fields and can have wavelengths that are about 100 times to about 500 times shorter than that of conventional light at the same frequency. For example, in a monolayer of silver decorated with adatoms, light can exist at the technologically important telecommunications frequency of 200 THz. For a conventional photon, this frequency corresponds to a wavelength of 1.5 μm. For this film of silver, this same frequency corresponds to a wavelength of only 4 nm, which is over 300 times shorter than that of the conventional photon and is close to the size of atoms.

This strongly confined 2D plasmon field near the surface of ultrathin conductors can be used to develop various applications, including light emitters, platforms for spectroscopic applications, organic light sources, and generation of broadband light with tunable bandwidth in visible and IR frequencies. In a spectroscopic platform, a sample is placed into a 2D plasmon field to interact with a probe beam (e.g., a laser beam). The interaction between the sample and the probe beam causes the sample to absorb spectral components in the probe beam via electronic transitions that are otherwise forbidden without the 2D plasmon. In broadband light generation applications, the strong two-plasmon spontaneous emission of emitters near ultrathin conductors is used to produce a broad spectrum of light. For organic light sources, plasmons are used to quench excited triplet states, allowing fast singlet decay with the emission of light.

Plasmonic Spectroscopy Platforms

Figure 1:
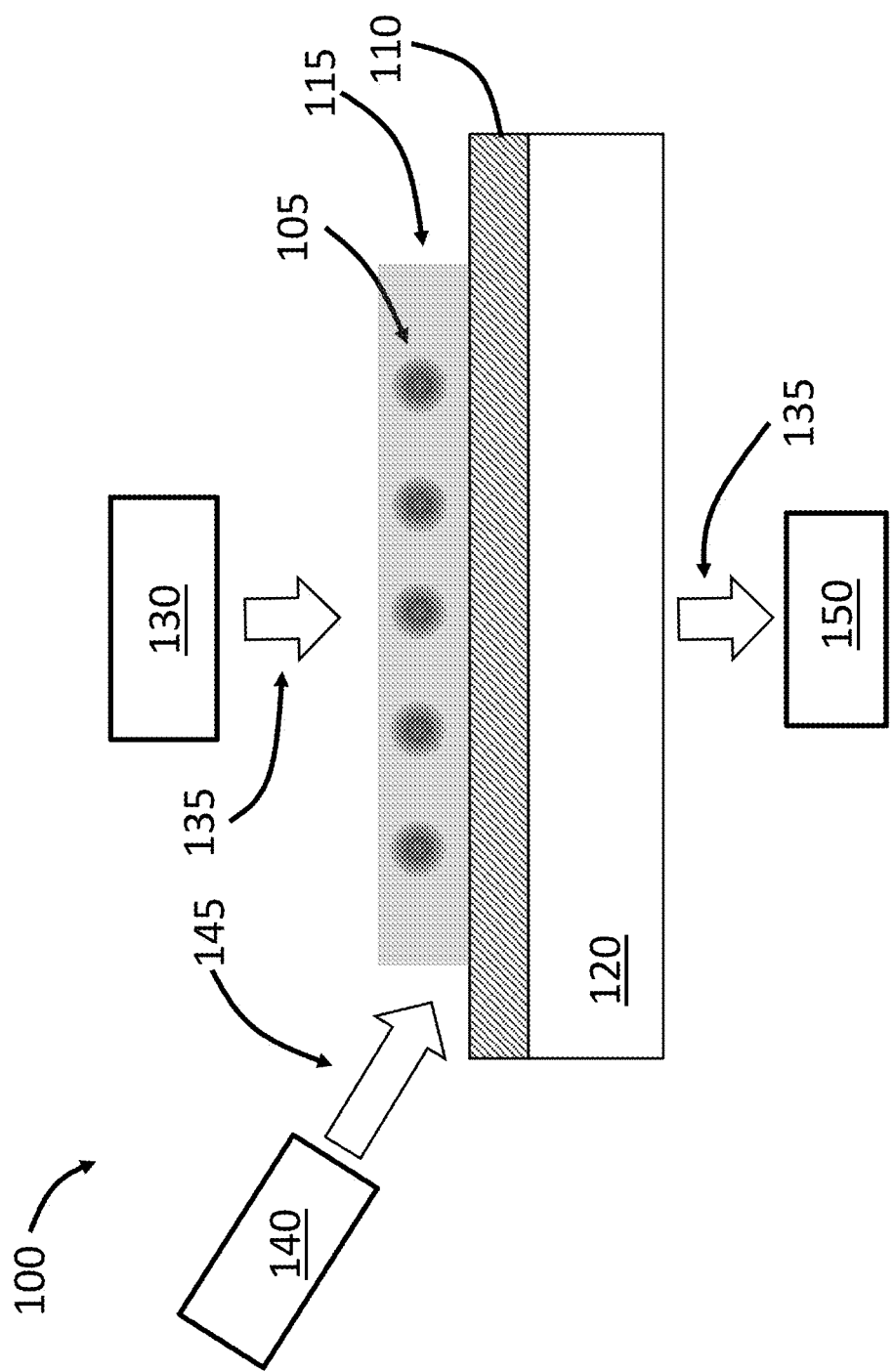
FIG. 1 shows a schematic of an apparatus for spectroscopy including an ultrathin conductor to generate plasmon fields.

FIG. 1 shows a schematic of an apparatus 100 for spectroscopy using an ultrathin conductor to generate plasmon fields. The apparatus 100 includes a conductive layer 110 disposed on a substrate 120. A radiation source 140 is disposed in radiative communication with the conductive layer 110 and emits an excitation beam 145 toward the conductive layer 110. The conductive layer 110 has a thickness less than 10 nm such that upon irradiation of the excitation beam 145, a plasmon field 115, such as a two-dimensional (2D) plasmon field, is generated near the surface of the conductive layer 110. A sample 105 is disposed in the plasmon field 115 and interacts with a probe beam 135 emitted by a light source 130, causing absorption of at least a portion of the probe beam 135. The absorption of the sample 105 can be achieved via transitions that are otherwise forbidden in the absence of the plasmon field 115. The apparatus 100 also includes a detector 150, in optical communication with the sample 105, to collect the probe beam 135 after the probe beam's interaction (e.g., scattering and/or absorption) with the sample 105. The detected change in the intensity and/or spectrum of the probe beam 135 can be used for identification of the transition, which in turn can be used to identify, for example, the material of the sample 105. The rate of absorption by the sample 105 can also be derived, thereby providing information about, for example, the concentration of the sample 105.

The conductive layer 110 can include any material that supports plasmon fields near its surface. In one example, the conductive layer 110 can include graphene. The graphene can include a monolayer of graphene, a bi-layer of graphene, or multilayer graphene. Due to the high mechanical strength of graphene, the conductive layer 110 can be suspended on a holder (i.e., the substrate 120 can be optional). In addition, the carrier density of graphene (e.g., electron density) can be conveniently adjusted by, for example, electrical gating. Alternatively or additionally, the carrier density of graphene can be adjusted by doping. Different carrier density can result in plasmons at different frequencies, thereby allowing the probing of different spectral bands in the sample 105.

In another example, the conductive layer 110 can include metal, such as silver, gold, and aluminum, among others. In yet another example, the conductive layer 110 can include $DySi_2$. In these examples, the conductive layer 110 can be supported by the substrate 120. In one example, the substrate 120 includes Si. In another example, the substrate 120 includes $Si_3N_4$. In yet another example, the substrate 120 includes $SiO_2$.

By using different materials for the conductive layer 110 or tuning the conduction electron density in the conductive layer 110, the frequency of the plasmon field 115 can be adjusted so as to cause the sample 105 to absorb radiation at different wavelengths. In one example, the sample 105 can absorb visible or near infrared light via electronic transitions. In another example, the sample 105 can absorb mid-infrared or far infrared light via vibrational transitions. The wavelength of spectral component absorbed by the sample 105 in the plasmon field 115 can be within a range of about 500 nm to about 10 µm (e.g., about 500 nm, about 750 nm, about 1 µm, about 2 µm, about 3 µm, about 4 µm, about 5 µm, about 6 µm, about 7 µm, about 8 µm, about 9 µm, or about 10 µm, including any values and sub ranges in between).

The sample 105 is disposed in the plasmon field 115 near the surface of the conductive layer 110. The distance between the sample 105 and the conductive layer 110 can be less than 30 nm (e.g., about 30 nm, about 25 nm, about 20 nm, about 15 nm, about 10 nm, about 8 nm, about 6 nm, about 4 nm, about 3 nm, or about 1 nm, including any values and sub ranges in between).

The sample 105 can be disposed in the plasmon field 115 by various means. In one example, the sample 105 can be disposed on a spacer layer, which is disposed on the conductive layer 110 (see, e.g., FIG. 4). The thickness of the spacer layer can be adjusted to control the distance between the sample 105 and the conductive layer 110. In another example, the sample 105 can be doped into a thin film disposed on the conductive layer 110 (see, e.g., FIG. 5). Doping the sample 105, such as atoms or molecules, into a thin film can incorporate a large population of absorbers into a volume that interacts with the probe beam 135, thereby increasing the sensitivity of the resulting spectroscopy. In yet another example, the sample 105 can be gaseous and delivered via gas flows into the plasmon field 115 (see, e.g., FIG. 6).

The light source 130 in the apparatus 100 is employed to provide the probe beam 135. In one example, the light source 130 can include a laser and the probe beam 135 can include a laser beam having a narrow linewidth (e.g., less than 1 GHz). The wavelength of the probe beam 135 can be close to a transition of interest, such as a signature transition of a material. In this case, the intensity of the probe beam 135 after interacting with the sample 105 can be used to detect the presence or absence of the material. The detector 150 can include a simple intensity detector such as a charge-coupled device (CCD) detector or a complementary metal-oxide-semiconductor (CMOS) detector.

In another example, the light source 130 can include a broadband light source and the probe beam 135 is accordingly broadband. This configuration can be advantageous when the composition of the sample is unknown. The detector 150 in this example can include a spectrometer to monitor the spectrum of the probe beam 135.

In one example, the probe beam 135 can be delivered to the sample 105 in free space. In another example, the probe beam 135 can be delivered to the sample 105 via one or more waveguides, including optical fibers. For example, the light source 130 can include a semiconductor laser also fabricated on the substrate 120 and transmit the probe beam 135 to the sample 105 via semiconductor waveguides (e.g., silicon or silicon oxide waveguides).

The radiation source 140 in the apparatus 100 is employed to provide the excitation beam 145 that generates the plasmon field 115 near the surface of the conductive layer 110. In one example, the radiation source 140 includes an optical light source and the excitation beam 145 includes an optical beam. In this case, one or more grating patterns can be fabricated into the conductive layer 110 to couple the incident excitation beam 145 into the conductive layer 110 and generate the plasmon field 115 (see, e.g., FIGS. 2A-2B).

In another example, metallic nanoparticles can be suspended above the surface of the conductive layer 110 as near-field sources. Alternatively, atoms can be used in place of nanoparticles. The nanoparticles or atoms can be excited with external light and then emit into plasmons, thus exciting a plasmon pulse.

In another example, the plasmon field 115 can be generated via direct near-field excitation. In this case, a conducive tip can be placed near the surface of the conductive layer 110 (e.g., within 30 nm) and the excitation beam 145 (e.g., an optical beam) can irradiate the conductive tip so as to generate the plasmon field 115. The conductive tip can include, for example, the tip of an atomic force microscope, such as that in a typical near-field scanning optical microscope (NSOM).

In yet another example, the radiation source 140 can include an electron source and the excitation beam 145 includes an electron beam. In this case, the plasmon field 115 can be generated via electron energy-loss spectroscopy, in which a high-energy electron beam impinges near the surface of the conductive layer 110 and transfers energy into propagating plasmons.

The detector 150 shown in FIG. 1 is disposed to receive the probe beam 135 after propagating through the conductive layer 110. In practice, the detector 150 can also be disposed at other locations. For example, the detector 150 can be disposed above the conductive layer 110 to collect light from the probe beam 135 that is reflected, scattered, or diffused by the conductive layer 110 and/or the sample 105.

The apparatus 100 as described above can examine the sample 105 via absorption spectroscopy. Alternatively, the apparatus 100 can be configured to examine the sample 105 via emission spectroscopy. For example, after the absorption of the probe beam 135 via transitions from a first energy state to a second energy state, the sample 105 can then relax back to the first energy state by emitting photons or plasmons. A detector can be used to detect this emission and estimate properties of the sample 105.

Figures 2A, 2B:
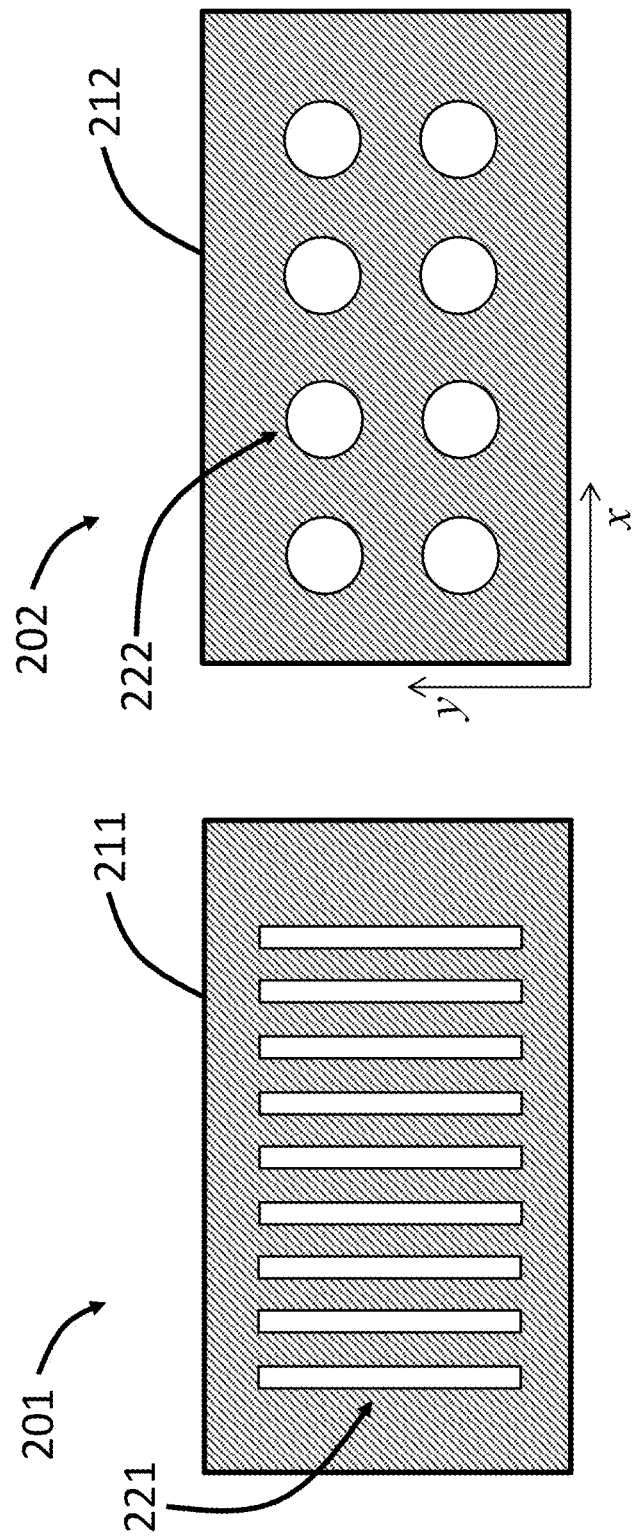
FIGS. 2A-2C illustrate patterns in or on ultrathin conductors to optically generate plasmon fields.

FIGS. 2A and 2B show top views conductive layers including fabricated patterns to facilitate the generation of plasmon field near the surface of the conductive layers. FIG. 2A shows a conductive layer 201 including a base layer 211 defining a grating 221, which can couple incident optical light into the conductive layer 201 and convert the incident optical light into plasmons. The pitch of the grating 221 can be about 5 nm to about 20 nm (e.g., about 5 nm, about 10 nm, about 15, nm, or about 20 nm, including any values and sub ranges in between).

FIG. 2B shows a conductive layer 202 including a base layer 212 defining a two-dimensional (2D) array of holes 222. This structure is also referred to as a 2D phononic crystal. In one example, the pitch of the holes 222 along the x direction is the same as the pitch of the holes 222 along they direction. In another example, the pitch of the holes 222 along the x direction can be different than the pitch of the holes 222 along they direction. The pitches along one or both directions can be about 5 nm to about 20 nm (e.g., about 5 nm, about 10 nm, about 15, nm, or about 20 nm, including any values and sub ranges in between).

The holes 222 shown in FIG. 2B have a round opening. In another example, the holes 222 can have a rectangular opening (including square). In yet another example, the holes 222 can have honeycomb shape. In yet another example, the holes 222 can have an elliptical opening. In yet another example, the holes 222 can have any other shape known in the art.

In one example, the holes 222 can be just openings (e.g., air holes). In another example, the holes 222 can be filled with a material having a refractive index different from the refractive index of the base layer 212.

Figure 2C:
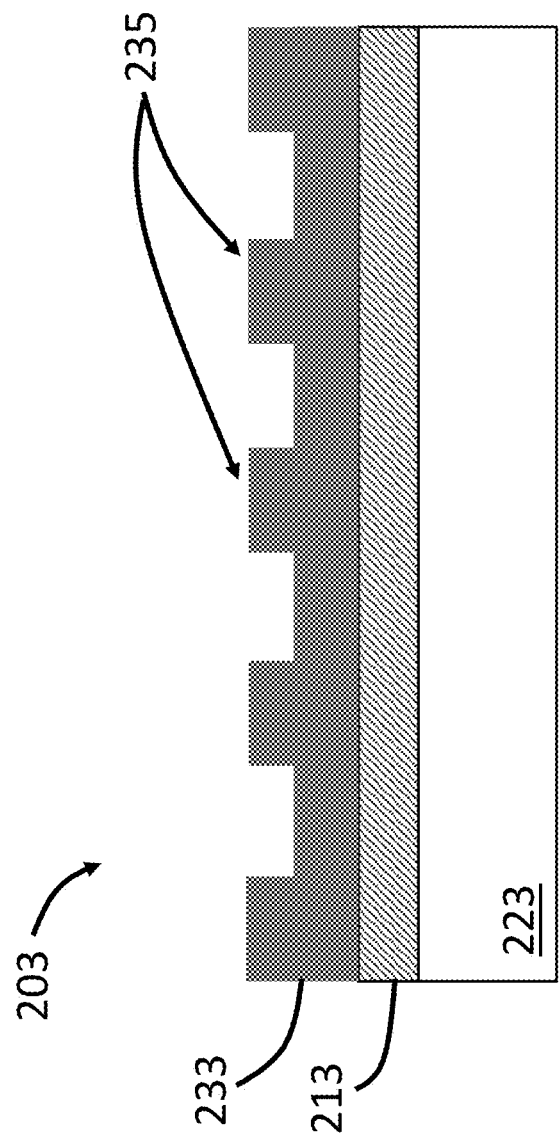

FIG. 2C shows sides view of apparatus 203 including a nano-antenna layer 233 disposed on a conductive layer 213, which in turn is disposed on a substrate 223. The nano-antenna layer 233 includes an array of nano-antennas 235, which can be made of, for example, silicon. The pitch of the array of nano-antennas 235 can be, for example, about 5 nm to about 20 nm (e.g., about 5 nm, about 10 nm, about 15 nm, or about 20 nm, including any values and sub ranges in between).

The grating 221, the holes 222, and the nano-antenna layer 233 can facilitate the coupling of external light into the conductive layers (i.e., 201, 202, and 213). They can also be employed to couple plasmons (e.g., emitted by samples near the surface of the conductive layers 201, 202, and 213) out of the conductive layers 201, 202, and 214. The plasmons coupled out by the grating 221, the holes 222, and/or the nano-antenna layer 233 can become far field radiation and can be collected by a detector to derive information of the sample.

Figure 3:
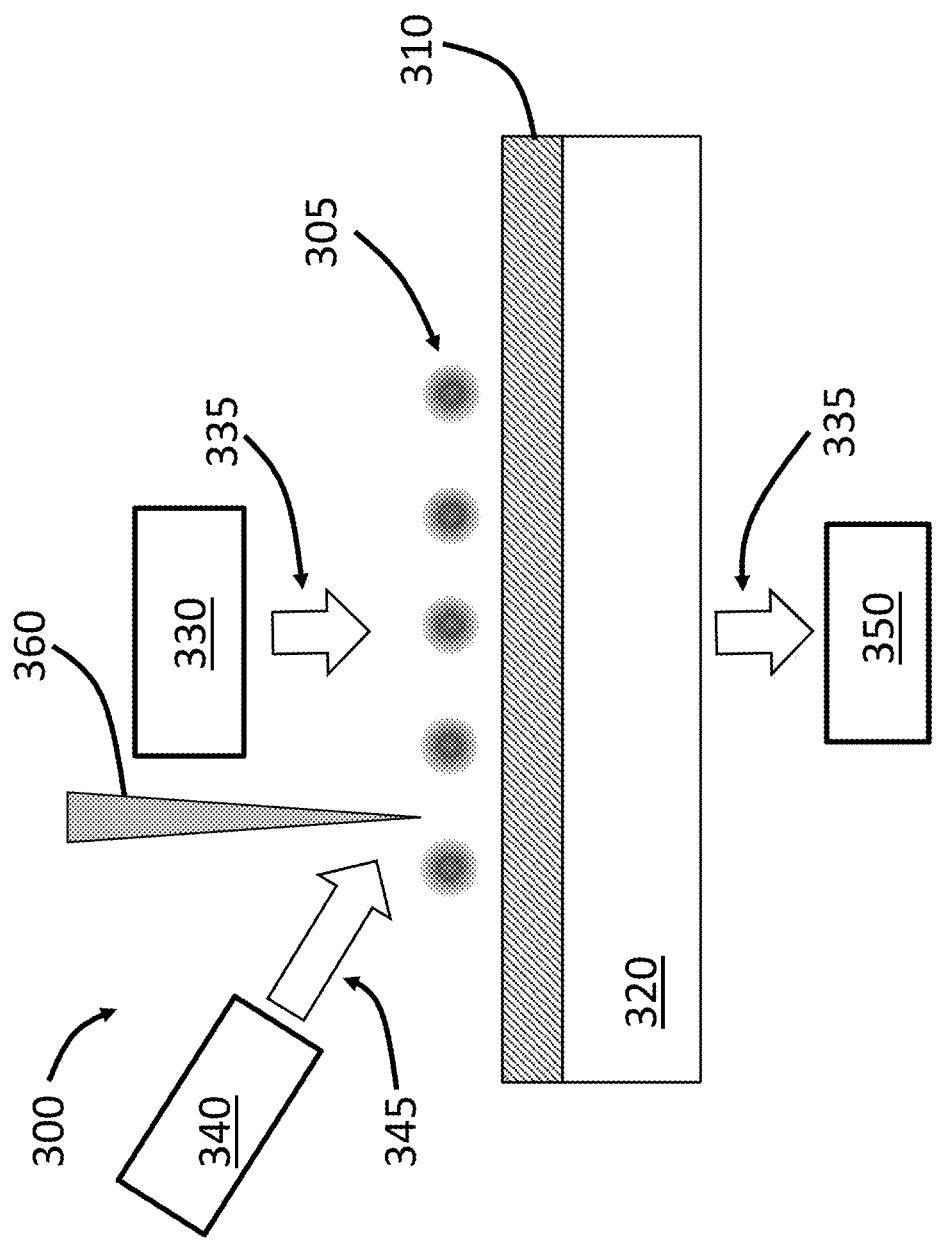
FIG. 3 shows a schematic of an apparatus for spectroscopy including a conductive tip to generate plasmon fields near the surface of an ultrathin conductor.

FIG. 3 shows a schematic of an apparatus 300 for spectroscopy including a conductive tip to generate plasmon fields near the surface of an ultrathin conductor. The apparatus 300 includes a conductive layer 310 disposed on a substrate 320. A conductive tip 360 is disposed near the surface of the conductive layer 310. A radiation source 340 emits an excitation beam 345 that irradiates the conductive tip 360, which can function as a near-field source. Such a source 340 can directly excite plasmon fields which propagate away from the tip 360. A sample 305 is disposed in the plasmon field and interacts with a probe beam 335 provided by a probe light source 330, causing absorption of at least one spectral component in the probe beam 335. A detector 350 is disposed to detect the probe beam 335 after interacting with the sample 305 for estimating properties of the sample 305.

In one example, the conductive tip 360 includes a metallic tip, such as a tungsten tip. In another example, the conductive tip 360 can include a base tip coated with a conductive material. The base tip can include, for example, a cleaved crystal, atomic force microscope (AFM) cantilever tip, semiconductor structure, or tapered optical fiber, among other things. The conductive coating can include, for example, silver, chromium, platinum, and carbon, among others. In this case, the conductive tip 360 can be substantially similar to the tip of a near-field scanning optical microscope (NSOM).

The distance between the conductive tip 350 and the surface of the conductive layer 310 can be less than 30 nm (e.g., about 30 nm, about 25 nm, about 20 nm, about 15 nm, about 10 nm, about 5 nm, or less, including any values and sub ranges in between).

Figure 4:
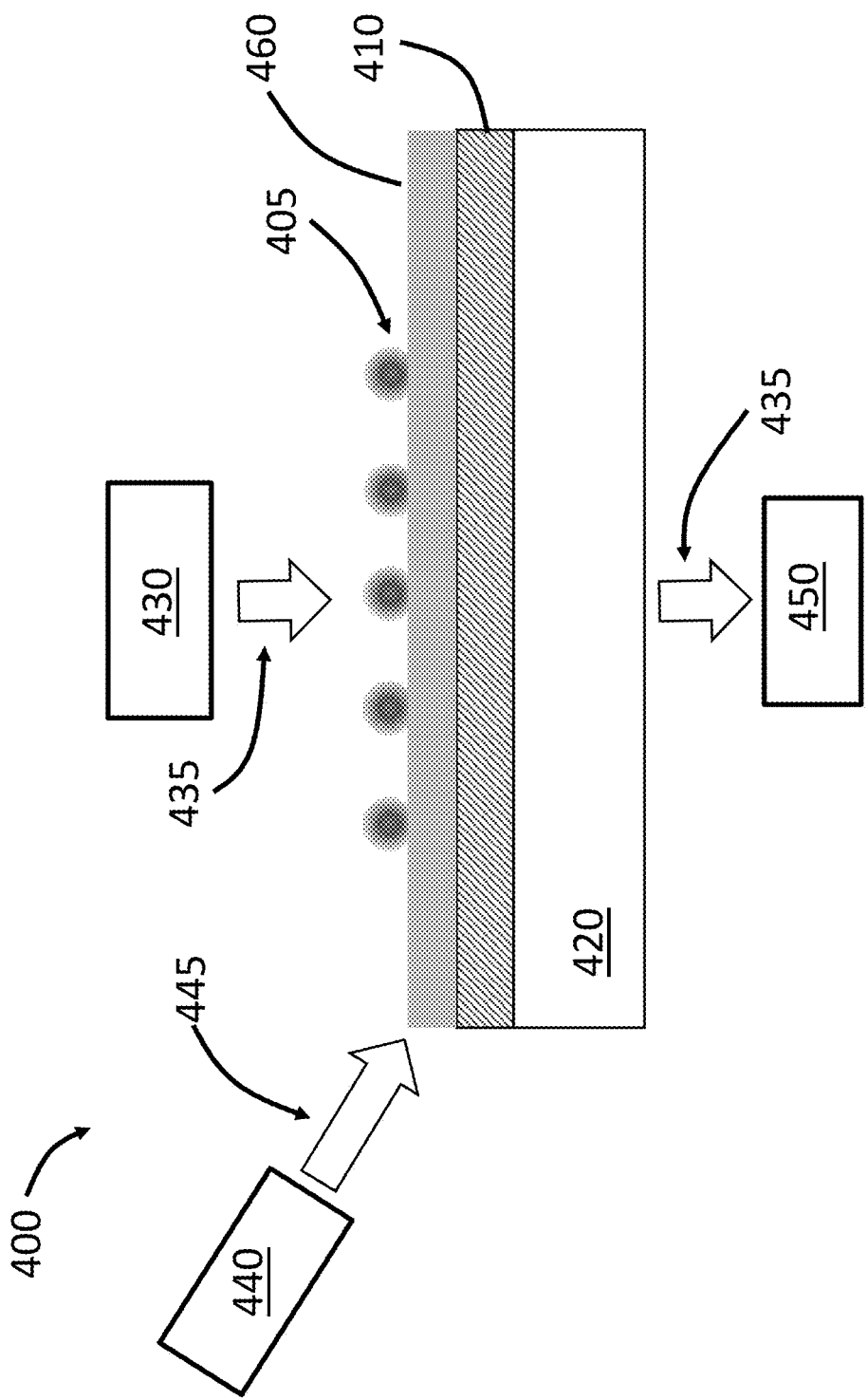
FIG. 4 shows a schematic of an apparatus for spectroscopy including a spacer layer to hold samples above an ultrathin conductor.

FIG. 4 shows a schematic of an apparatus 400 for spectroscopy including a spacer layer 460 to hold a sample 405 above a conductive layer 410 on a substrate 420. The spacer layer 460 can include materials that are chemical inert relative to the conductive layer 410 and the sample 405 so as to reduce the probability of distorting spectral lines of the sample 405. For example, the spacer layer 460 can include aluminum oxide. A radiation source 440 is in radiative communication with the conductive layer 410 so as to generate plasmon fields near the surface of the conductive layer 410 via an excitation beam 445. A light source 430 is disposed in optical communication with the sample 405 and delivers a probe beam 435 to interact with the sample 405 in the plasmon fields generated by the excitation beam 445. A detector 450 is in optical communication with the sample 405 to collect the probe beam 435 after interacting with the sample 405.

In one example, the spacer layer 460 can be removable, in which case different spacer layers 460 can be disposed on the conductive layer 410 in different applications. In another example, the spacer layer 460 can be a thin film deposited on the conductive layer 410 via, for example, physical vapor deposition, chemical vapor deposition, or any other deposition techniques known in the art.

The thickness of the spacer layer 460 adjusted to change the distance between the sample 405 and the conductive layer 410. In practice, the thickness of the spacer layer 460 can be about 5 nm to about 20 nm (e.g., about 5 nm, about 10 nm, about 15, nm, or about 20 nm, including any values and sub ranges in between). Using the spacer layer 460 can keep the sample 405 at controlled distances relative to the conductive layer 410.

Figure 5:
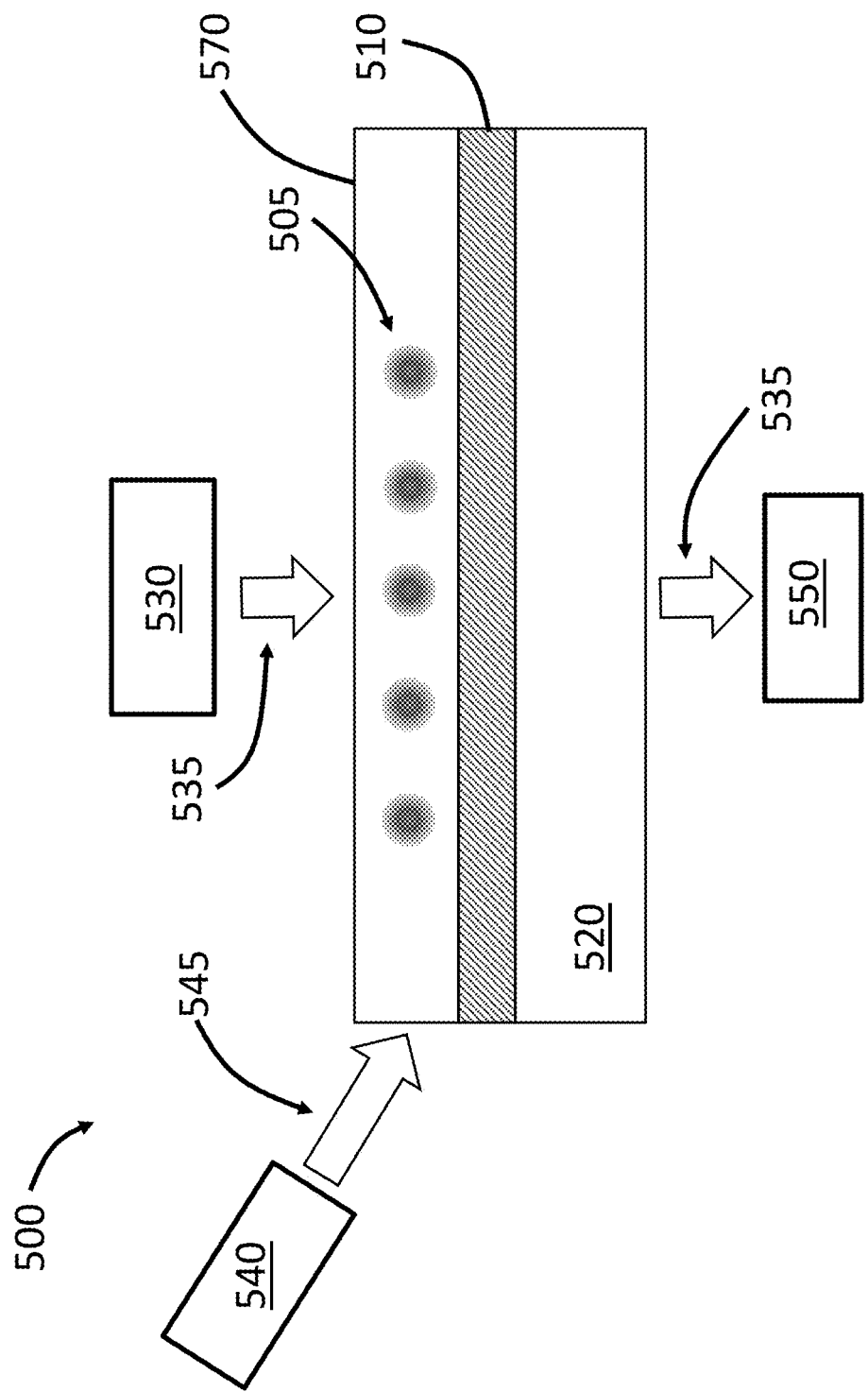
FIG. 5 shows a schematic of an apparatus for spectroscopy where samples are doped into a sample layer.

FIG. 5 shows a schematic of an apparatus 500 for spectroscopy where a sample 505 is doped into a sample layer 570, which in turn is disposed on a conductive layer 510 on a substrate 520. A radiation source 540 is in radiative communication with the conductive layer 510 to generate plasmon fields near the surface of the conductive layer 510 via an excitation beam 545. A light source 530 is disposed in optical communication with the sample 505 and delivers a probe beam 535 to interact with the sample 505 in the plasmon fields generated by the excitation beam 545. A detector 550 is in optical communication with the sample 505 to collect the probe beam 535 after interacting with the sample 505.

The sample 505 can include sample particles disposed into an array. The sample particles can include, for example, atoms, molecules, quantum dots, quantum wells, or quantum wires, among others. For example, the array can be a 2D array. In other words, the sample particles can be disposed on a same plane (e.g., shown in FIG. 5). In another example, the array is a 3D array, in which case the sample particles can be stacked over each other. This configuration can increase the interaction length between the probe beam 535 and the sample 505.

Figure 6:
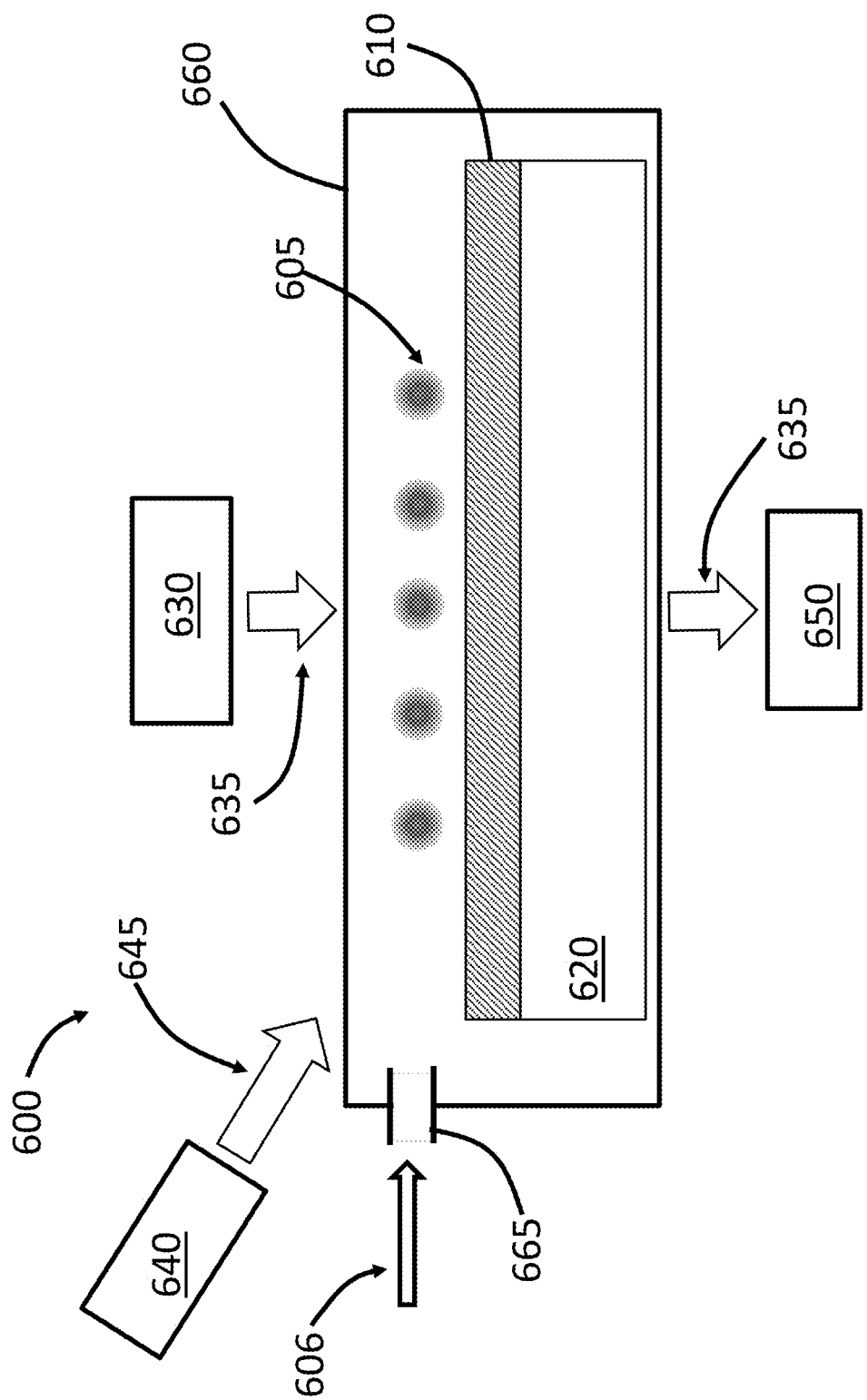
FIG. 6 shows a schematic of an apparatus for spectroscopy including a chamber to receive gaseous samples.

FIG. 6 shows a schematic of an apparatus 600 for spectroscopy including a chamber 660 to receive a gaseous sample 605. The chamber 660 includes an entry port 665 to receive a gas flow 606 that includes the gases sample 605. The gaseous sample 605 is delivered to locations near the surface of a conductive layer 610 disposed on a substrate 620. A radiation source 640 is in radiative communication with the conductive layer 610 to generate plasmon fields near the surface of the conductive layer 610 via an excitation beam 645. A light source 630 is disposed in optical communication with the sample 605 and delivers a probe beam 635 to interact with the sample 605 in the plasmon fields generated by the excitation beam 645. A detector 650 is in optical communication with the sample 605 to collect the probe beam 635 after interacting with the sample 605. The apparatus 600 can also be configured for liquid samples. In this case, a pump (not shown in FIG. 6) can pump microfluid flow 606 into the chamber 660 so as to provide the sample 605.

Broadband Light Generation Using Plasmon Fields

Figure 7A:
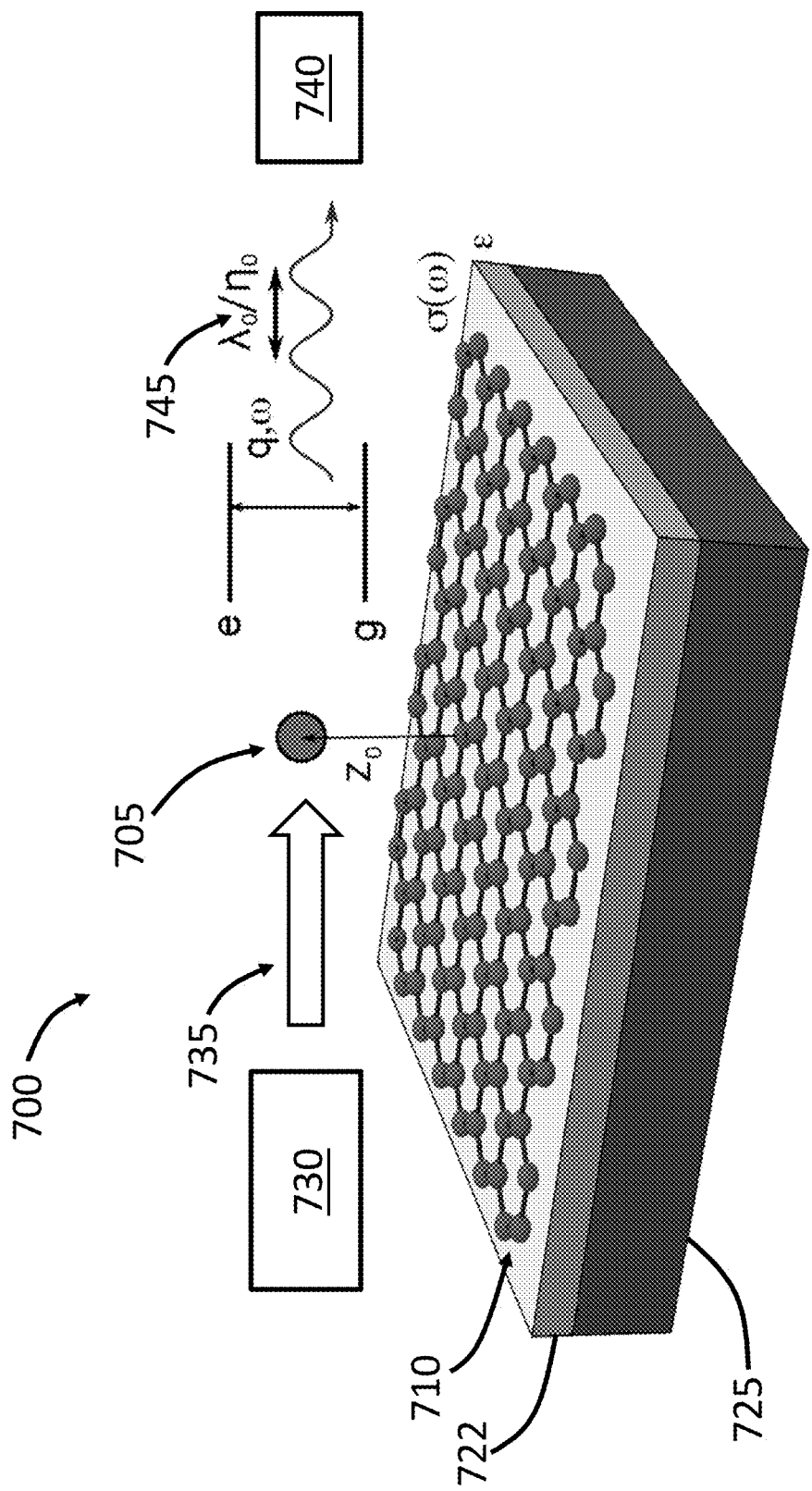
FIG. 7A shows a schematic of an apparatus for broadband light generation using plasmon fields near the surface of an ultrathin conductor.
Figure 7B:
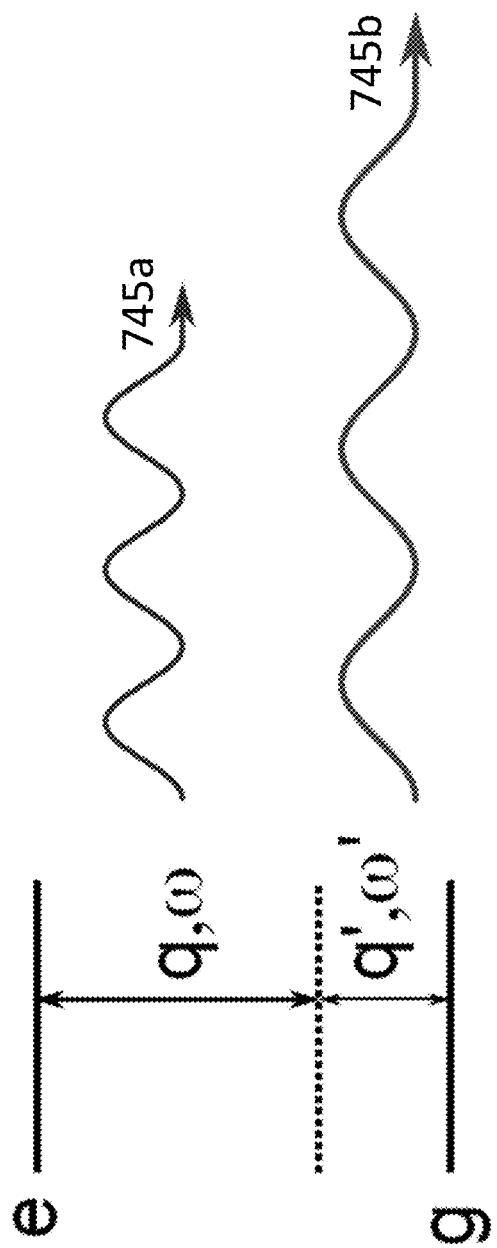
FIG. 7B shows a schematic of energy level diagram for two-plasmon spontaneous emission that can be used in the apparatus shown in FIG. 7A.

Plasmon fields near the surface of a thin conductor can also be used to develop broadband light sources. FIG. 7A shows a schematic of an apparatus 700 for broadband light generation using plasmon fields near the surface of a conductive layer 710. FIG. 7B shows a schematic of energy level diagram for two-plasmon spontaneous emission that can be used in the apparatus 700 shown in FIG. 7A.

The apparatus 700 includes an emitter 705 disposed near the surface of the conductive layer 710. The distance $z_0$ between the emitter 705 and the conductive layer 710 can be about 5 nm to about 20 nm (e.g., about 5 nm, about 10 nm, about 15, nm, or about 20 nm, including any values and sub ranges in between). A light source 730 is in optical communication with the emitter 705 and irradiates the emitter 705 with an input light beam 735. The input light beam 735 can be monochromatic and excites the emitter 705 from a first energy state (e.g., ground state g in FIG. 7B) to a second energy state (e.g., excited state e in FIG. 7B).

In the presence of 2D plasmon fields near the surface of the conductive layer 710, the emitter can relax by emitting two plasmons 745a and 745b, schematically illustrated in FIG. 7B. In two-plasmon emission, the emitted light can have photon energy anywhere between zero and the transition energy (i.e., the energy gap between the ground state and the excited state), thereby providing emission with a broad spectrum. The emitter 705 can relax on a timescale that is strongly tunable by controlling the distance between the emitter 705 and the conductive layer 710. Generally, a larger distance can lead to a longer timescale.

The apparatus 700 can include an optional detector 740 to detect the emission 745. In this case, the conductive layer 710 can include a grating or photonic crystal structure to couple the plasmons out of the conductive layer 710 and into the far field. The grating or photonic crystal structure can be substantially similar to those described above with reference to FIGS. 2A and 2B.

The emitter 705 can include atoms, molecules, quantum dots, or thin films, among other things. For example, the emitter 705 can include multiple atoms, molecules, quantum dots, or any other type of emitter, which are embedded into a thin film. The thin film, in turn, is disposed on the conductive layer 710. In another example, the emitter 705 can be disposed on a spacer layer that is disposed on the conductive layer 710, in a manner similar to that shown in FIG. 4.

The conductive layer 710 can be substantially similar to the conductive layers 110, 310, 410, 510, and 610 described above with reference to FIG. 1 and FIGS. 3-6. For example, the conductive layer 710 can include graphene, silver, gold, or $DySi_2$. In FIG. 7A, the conductive layer 710 is disposed on an optional spacer layer 722 and an optional substrate 725. The spacer layer 722 and the substrate 725 can include, for example, silicon, silicon oxide, or silicon nitride.

The apparatus 700 can deliver broadband light 745 using a single frequency input beam 735. An advantage of the apparatus 700 is that the apparatus 700 can be configured into a nanoscale system. In addition, the apparatus 700 also has a wide degree of tunability in terms of generation rates and spectral shape of the output emission. This technique can be performed at many frequency scales from the visible to the far-IR.

For example, the input light 735 can be monochromatic and photon energy in the input light 735 can be substantially close to the energy gap between the ground state and the excited state of the emitter 705. In another example, the input light 735 can be broadband (e.g., provided by a light emitted diode). In yet another example, the emitter 705 can be excited through simultaneous absorption of a photon (e.g., from a laser) and a plasmon (e.g., generated through any of the methods described above). An advantage of this form of excitation is that it allows the observation of transitions with high energy and high angular momentum using currently existing technology.

Generation of Entangled Plasmon Pairs

The apparatus 700 can be configured to generate entangled light at rates more than 10 orders of magnitude faster than conventional entangled photon generation. For example, the quantum efficiency of generating entangled plasmon emission can reach nearly 10%, whereas the typical efficiencies of entangled photon generation are around one one-millionth of a percent.

In the apparatus 700, the emitter 705 can include a quantum dot, quantum well, nitrogen vacancy center, or superconducting qubit. To increase the efficiency of entangled photon generation, the emitter 705 can satisfy two conditions. First, the two-photon transition energy (i.e., the energy gap between the ground state and excited state shown in FIG. 7B) of the emitter 705 can be within the spectral gap of the conductive layer 710, (e.g., a graphene layer). The spectral gap of graphene is a frequency region where the graphene has a very limited capacity to enhance spontaneous emission (also referred to as intra-band regime). This gap region is typically a function of the doping level (Fermi Energy) of graphene. As a result, for a random emitter, this technique can be realized by changing the doping of graphene. Second, half of the transition energy can experience strong Purcell enhancement due to plasmons. Under these two conditions, the two-plasmon spontaneous emission can experience an enhancement relative to competing one-photon processes that can be in excess of 8 orders of magnitude, almost completely bridging the gap between first-order and second-order emission processes.

Alternatively, another way to achieve very high efficiency generation of two or more entangled plasmons is using plasmonic crystals (also referred to as plasmonic metamaterials) to replace the conductive layer 710 in the apparatus 700. A plasmonic crystal can include a graphene layer including a two-dimensional periodical pattern (e.g., like the pattern in FIG. 2B) to open up a bandgap for which no plasmonic modes exist. In one example, the plasmonic crystal includes periodic arrays of air holes in a square or hexagonal lattice in a graphene layer. In another example, the plasmonic crystal can include periodic arrays of air holes in a square or hexagonal lattice in a superstrate or substrate disposed on a graphene layer.

Taking an emitter with two energy levels separated by a frequency in the plasmonic band gap (but half the frequency is not in the bandgap) can significantly (up to loss-broadening) enhance the two-plasmon emission relative to the emission at first order, in a manner similar to that described above. If the difference in energy of the two levels is in the plasmonic bandgap, and the plasmonic crystal were completely non-dissipative (i.e., no loss-broadening), then one-plasmon decay would be negligibly enhanced as discussed above. On the other hand, if half the energy difference of the levels is not in the bandgap, then it is strongly enhanced by plasmons and thus can happen very fast (e.g., on a time scale as fast as or even faster than one-plasmon decay).

Plasmonics for Electrical and Chemical Tuning of Far-Field Spectrum

Plasmons can also be used to reshape spectral properties of emitters, even when the resulting plasmons are not coupled out. When a highly excited electron in an emitter (e.g., atom, molecule, quantum dot, quantum well, superconducting qubit, etc.) decays via forbidden transitions, the path of states that it traverses to get to the ground state can be completely modified. As a result, the transitions (for example, at high frequency) which occur primarily through far-field radiation can be modified. Thus, the far-field photon spectrum of the emitter can be modified by the presence of forbidden transitions.

This principle can also be used to realize the spectroscopic applications described above (e.g., FIGS. 1-6). For example, consider a dilute (solid) solution of emitters in a thin film placed on top of a 2D plasmonic platform like doped graphene. One way to excite the emitters is using an external light-source. Once excited, the emitters can decay via a probabilistic path towards their ground states. Some of these paths, due to the allowing of forbidden transitions, can result in new far-field photons. These photons can be collected (for example, via a confocal microscope), and the number of photons collected can be compared to the prediction of the decay pathways of electrons (from the rate equations) to quantitatively infer the presence of forbidden transitions.

Moreover, it is also possible to reshape the spectrum of an emitter using the Lamb shift. In the presence of a nanophotonic structure like a 2D-plasmon or phonon-polariton supporting surface, one can shift the energy levels of nearby emitters, changing the frequencies at which they emit light.

Methods of Spectroscopy Using Plasmon Fields

Figure 8:
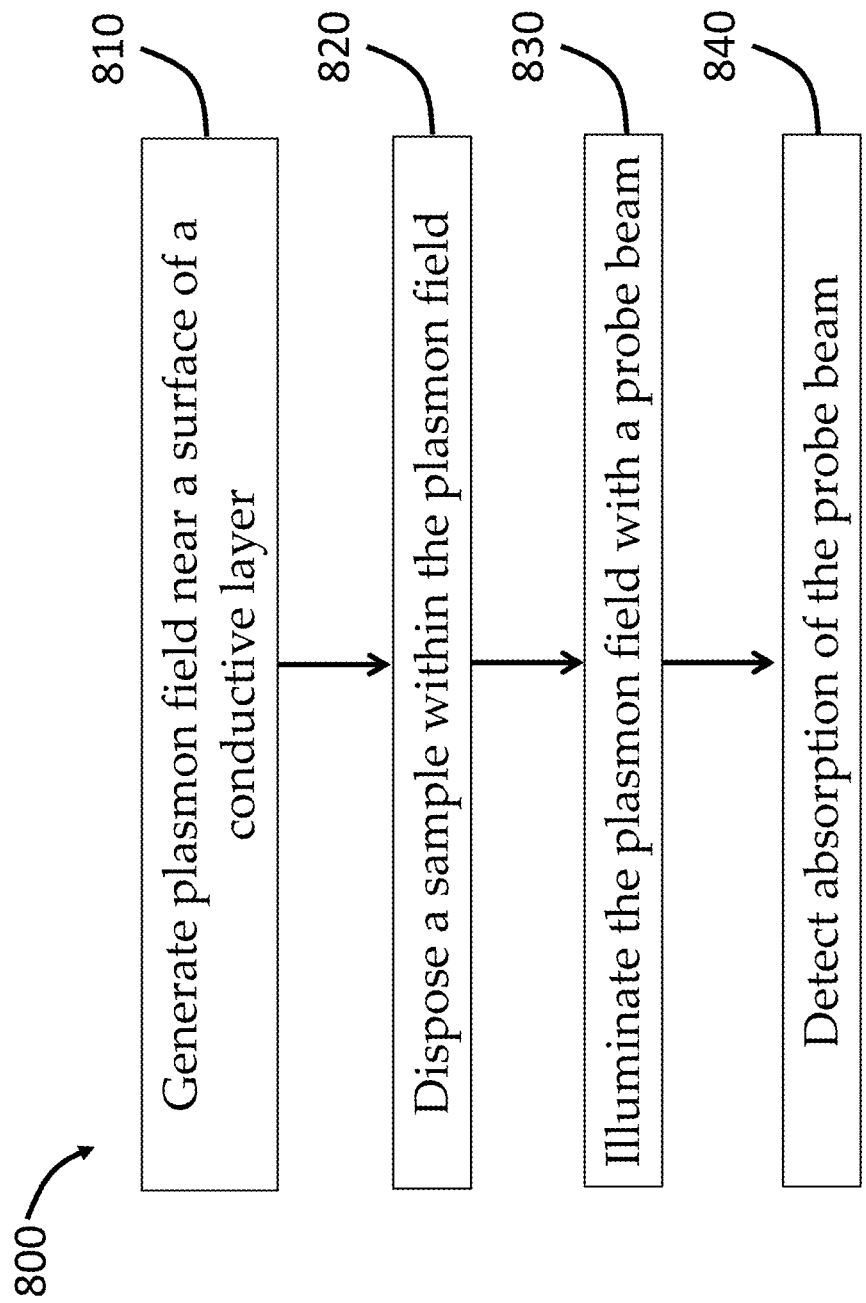
FIG. 8 illustrates a method of spectroscopy using plasmon fields.

FIG. 8 illustrates a method 800 for spectroscopy using plasmon fields. The method 800 includes generating a two-dimensional (2D) plasmon field near a surface of a conductive layer having a thickness less than 5 nm at step 810. At step 820, a sample to be examined is disposed in the 2D plasmon field. The method also includes illuminating the 2D plasmon field with a probe beam, causing the sample to absorb at least one spectral component in the probe beam, at step 830. The absorption of the spectral component is then detected at step 840.

In one example, creation of the 2D plasmon field at step 810 can be achieved by coupling a light beam into the conductive layer via a grating fabricated in the conductive layer. The grating can have a period of about 5 nm to about 20 nm (e.g., about 5 nm, about 10 nm, about 15, nm, or about 20 nm, including any values and sub ranges in between). In another example, the 2D plasmon field can be created by irradiating a conductive tip disposed at a distance less than 10 nm away from the surface of the conductive layer. The conductive tip can function as a near-field source to generate and propagate the 2D plasmon field near the surface of the conductive layer.

In one example, the sample is introduced into the 2D plasmon field by disposing the sample onto a spacer layer disposed on the conductive layer. The spacer layer can have a thickness less than 10 nm. In another example, the sample can be gaseous and can be disposed into the 2D plasmon field by flowing the sample in a gaseous state to a chamber containing the conductive layer.

Methods of Broadband Light Generation Using Plasmon Fields

Figure 9:
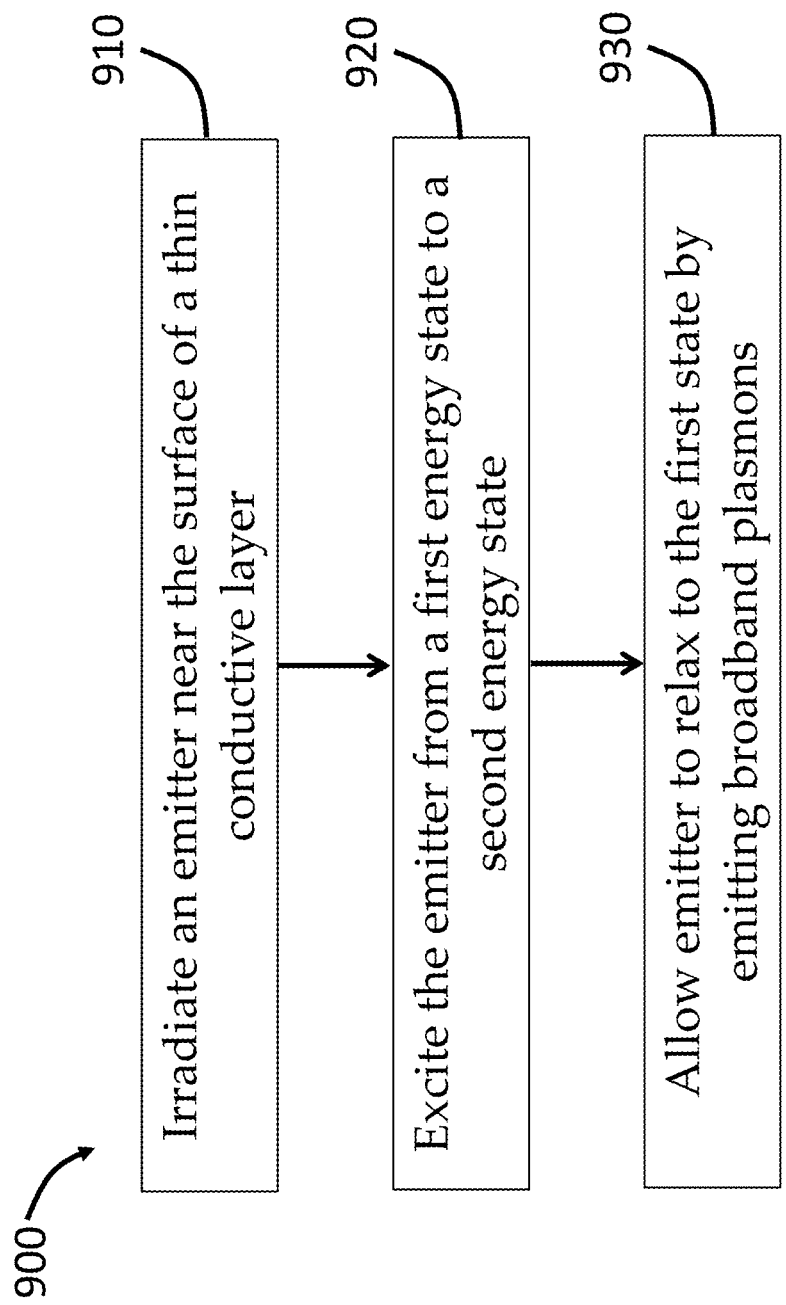
FIG. 9 illustrates a method of broadband light generation using plasmon fields.

FIG. 9 illustrates a method 900 of generating broadband emission using plasmon fields near the surface of a thin conductor. The method 900 includes irradiating, with a monochromatic light beam, an emitter disposed at a distance less than 10 nm away from a surface of a conductive layer having a thickness less than 5 nm, at step 910. Upon irradiation of the monochromatic light beam, the emitter is excited from a first energy state to a second energy state at step 920. The emitter relaxes to the first energy state at step 930, emitting at least two plasmons in the process. Each plasmon can have a photon energy anywhere between zero and the energy gap between the first energy state and the second energy state, thereby providing a broadband emission.

The emitter as used in method 900 can include multiple emitters, such as atoms, molecules, quantum dots, quantum wells, superconducting qubit, nitrogen vacancy centers, or any other type of emitters, so as to increase the power of the emission. In one example, the multiple emitters are embedded in a substrate disposed on the conductive layer. In another example, the multiple emitters are disposed on a spacer layer that is disposed on the conductive layer.

In one example, the conductive layer can include a grating (e.g., fabricated in the conductive layer) to couple the emitted plasmons out of the conductive layer as far field radiation. In another example, a prism can be used to couple the emitted plasmons out of the conductive layer as far field radiation. The prism as used herein can be referred to any kind of nanostructure and can be placed either on top of a spacer layer (if present) or on top of the conductive layer.

The method 900 can further include a step of changing the distance between the emitter and the conductive layer so as to the emission rate and/or the emission bandwidth. In one example, the emitter is disposed on a spacer layer. Different spacer layers (having different thicknesses) can be used to achieve different distances between the emitter and the conductive layer. In another example, the emitters can be pre-embedded into substrates at different distances away from the bottom of the substrate. In operation, different substrates can be placed on the conductive layer to achieve different distances between the emitter and the conductive layer.

Quenching of Triplet States

Other than spectroscopy and broadband light generation, plasmon fields near the surface of a thin conductor can also be used to quench triplet states. Conventional quenchers that reduce the lifetime of excited triplet states usually have a number of undesirable features, including short lifetimes, high toxicity, and low tunability (compared to the rate of quenching). Conventional quenchers are also usually in liquid form and stored in low-temperature (e.g., −20° C.) and low-oxygen environments.

Using plasmon fields for triplet quenching can address, at least partially, the challenges mentioned above. In general, triplet quenching can be implemented by replacing the sample 105 in FIG. 1 by the molecules to be quenched. For example, singlet-triplet molecules can be placed near a 2D plasmon-supporting surface, such as the surface of a thin conductive layer. Materials of the conductive layer can include graphene, silver, gold, $DySi_2$, or any other existing 2D plasmonic material which supports plasmons at the desired frequency. The substrate options are also the same as those described above with reference to FIG. 1. Without the plasmon field, molecules in an excited singlet state usually perform an intersystem crossing into the triplet state and remain stuck in the triplet state due to its long lifetime. In the presence of plasmon fields, however, the molecules can quench through the spontaneous emission of a plasmon at rates comparable to those of conventional molecular quenchers, but without the limitations of conventional quenchers.

Strong Confinement of Light Fields in Other Platforms

In descriptions above, plasmon fields are generated near the surface of a thin conductive layer. At least two other methods can also be used to generate plasmon fields for implementing the techniques described above.

In one example, a nano-antenna can be used to confine light on the scale of about 1 nm. For example, a bow-tie antenna can be used to confine electromagnetic fields in the gap between a bow-tie shaped piece of metal typically made out of silver, gold, aluminum, and other common plasmonic materials. This bow-tie antenna can replace the conductive layers (e.g., 110 and 310 to 710 shown in FIG. 1 and FIGS. 3-7) to achieve same functions in the apparatus (e.g., 100 and 300-700 shown in FIG. 1 and FIGS. 3-7).

In another example, a pure dielectric layer can be patterned on the scale of nanometers using, for example, standard lithographic techniques. The nanoscale patterning can force electromagnetic fields to vary on the scale of nanometers. As a result, local confinement of electromagnetic fields can also be achieved.

Simulation Characterization of Plasmon Fields Applications

Figure 10:
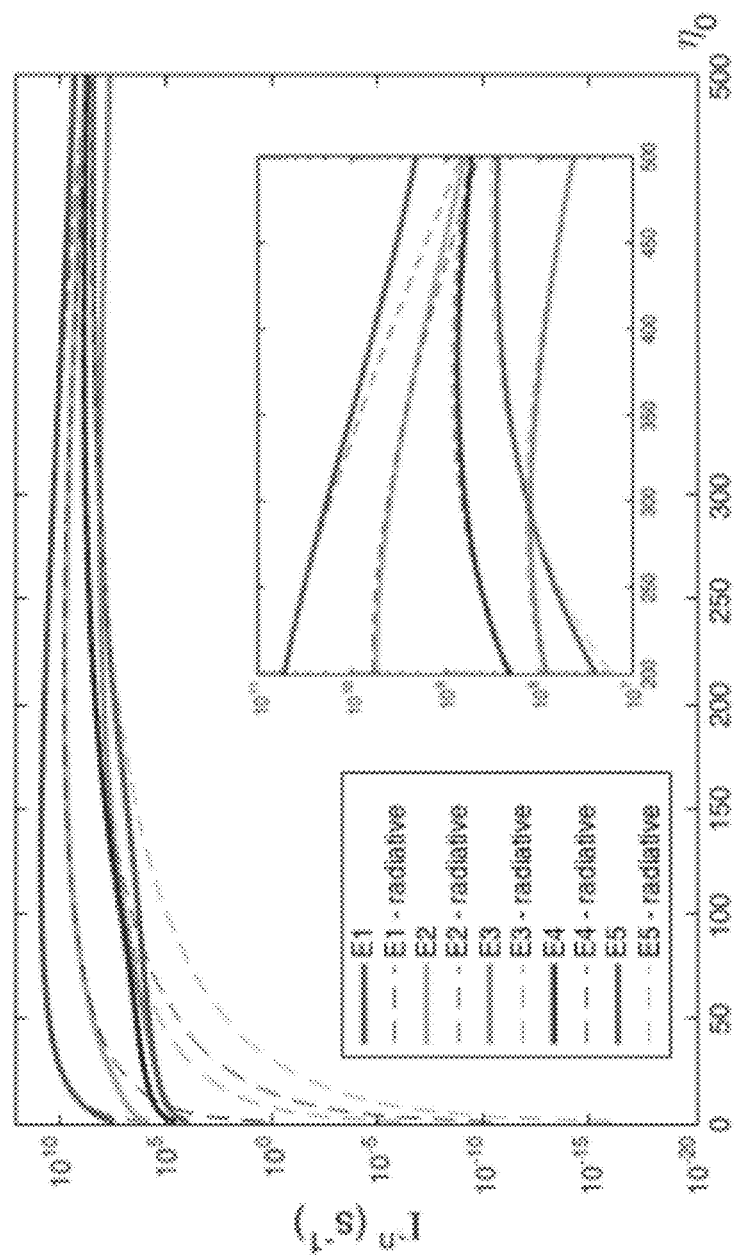
FIG. 10 shows calculated absorption rates of various multipolar transitions in hydrogen disposed in a plasmon field as a function confinement of the plasmon that can be varied by changing the conduction electron density.

FIG. 10 shows calculated absorption rates of various multipolar transitions in hydrogen disposed in a plasmon field as a function confinement of the plasmon that can be varied by changing the conduction electron density. These transitions include this E1 transition (electronic dipole transition), E2 transition (electronic quadruple transition), E3 transition (electronic octupole transition), E4 transition (electronic hexadecupole transition), and E5 transition (32-pole transition). FIG. 10 shows that the otherwise unobservable processes can occur in 2D plasmon systems at rates that are fast enough to make a spectroscopy platform (e.g., apparatus 100 shown in FIG. 1). By measuring how much light is absorbed, one may uniquely infer both the transition and the rate of transition. The absorbed light can be directly measured using a near-field probe such as a near-field optical scanning microscope (NSOM).

Figures 11A, 11B:
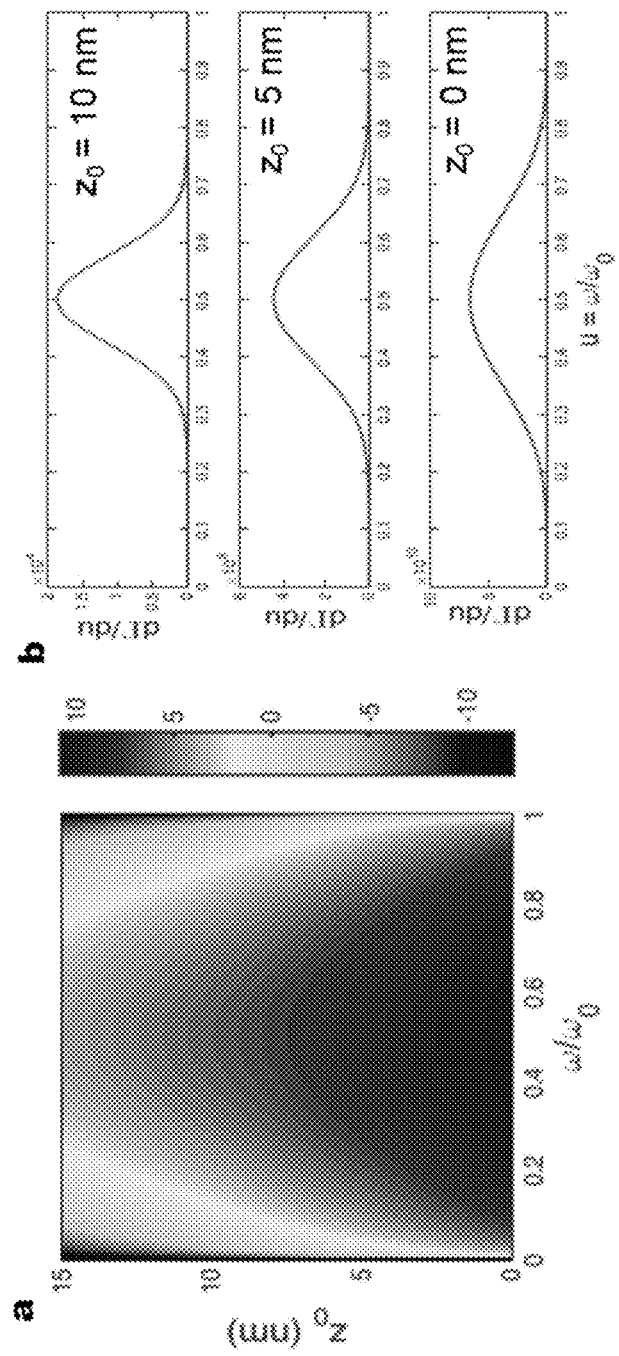
FIG. 11A shows calculated rates of two-plasmon spontaneous emission of an atom near the surface of a thin conductor.
FIG. 11B shows emission spectra of an emitter near the surface of a thin conductor at different emitter-surface separations.

FIG. 11A shows calculated rates of two-plasmon spontaneous emission of an atom near the surface of a thin conductor. FIG. 11B shows emission spectra of an emitter near the surface of a thin conductor at different emitter-surface separations, demonstrating a method to precisely control the distribution of emitted light. Controlling the distance between the surface and the emitter allows not only tunability of the rate of broadband light generation, but also tunability of the width of the distribution of emitted light (see FIG. 11B). As the separation increases from 0 to about 10 nm, the linewidth of the emitted light decreases monotonically.

Figures 12A, 12B:
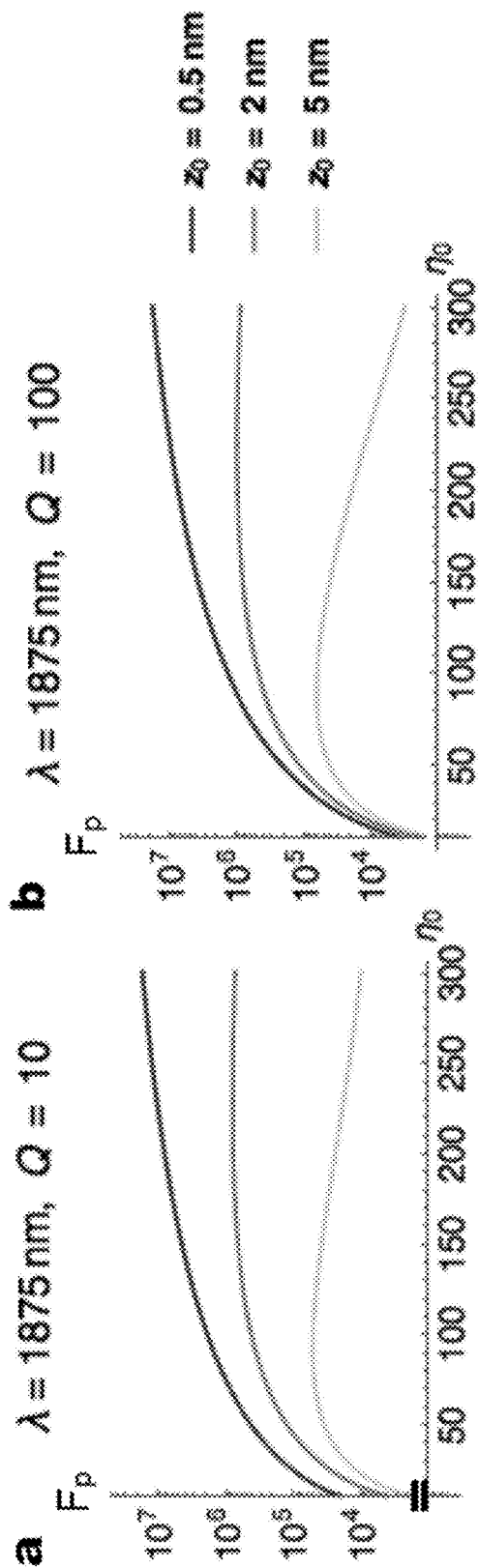
FIGS. 12A-12D show calculated enhancement factors for a singlet-triplet transition to demonstrate quenching of triplet states.
Figures 12C, 12D:
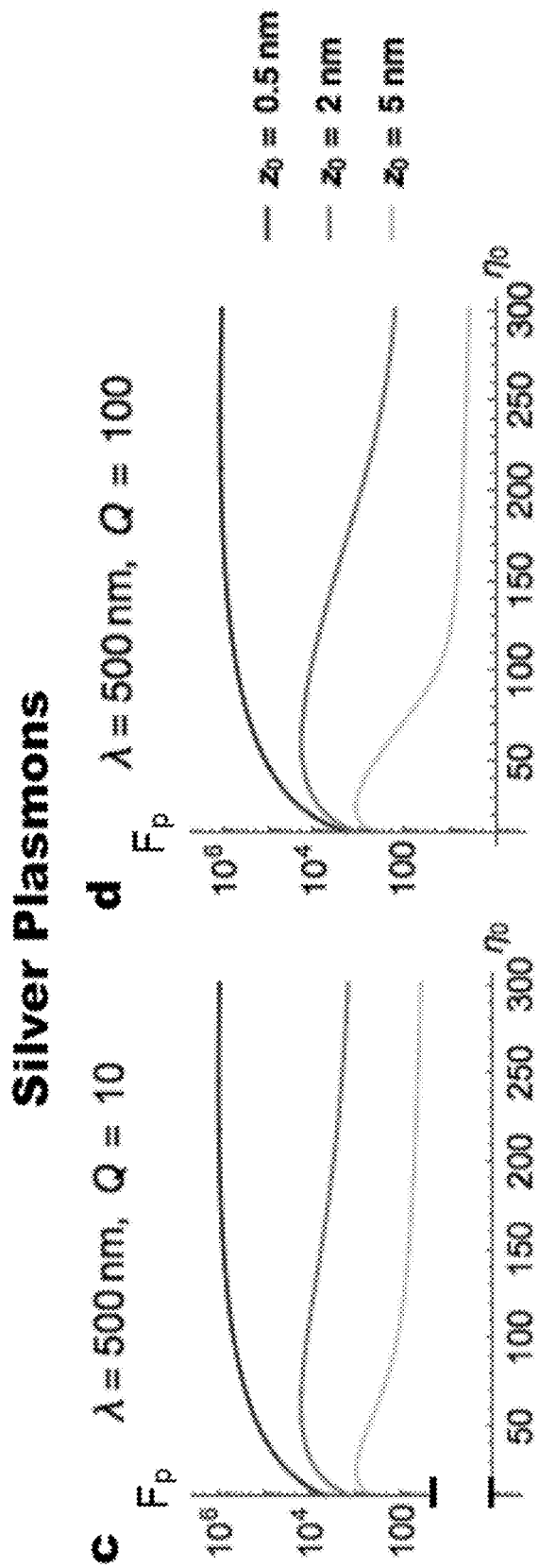

FIGS. 12A-12D show calculated enhancement factors as a function of conduction electron density for a singlet-triplet transition to demonstrate quenching of triplet states. FIGS. 12A and 12B show calculated enhancement factors of a single-triplet transition of an emitter placed near a graphene surface with a quality factor (Q) of 10 and 100, respectively. The quality factor can be defined as the number of periods of oscillation of the plasmon before its intensity decays by 1/e (e~2.718). FIGS. 12C and 12D show calculated enhancement factors of a single-triplet transition of an emitter placed near a silver surface with a quality of 10 and 100, respectively. The rate at which a triplet state can be quenched is tunable electronically by varying the conduction electron density of the surface. In practice, this can be achieved by applying a voltage to the surface, e.g., via electrodes coupled to a voltage source. FIGS. 12A-12D show that the quenching rate can be tuned by many orders of magnitude. Another important advantage of using plasmon fields for quenching is that this technique can be complementary to existing approaches used to reduce the lifetime of triplet states, such as increasing spin-orbit coupling and energy inversion of excited triplet and singlet states.

Turning Forbidden Transitions into Dominant Transitions

As described above, plasmons can be observed in 2D conductors and strongly confined over a broad spectral band, thereby providing access to transitions that are otherwise too slow to be observable. These forbidden transitions can, for example, include high-order multipole transitions, two-plasmon spontaneous emission processes, and spin-flip phosphorescence processes. Out of this broadband enhancement of forbidden transitions, it can also be beneficial to select a particular forbidden transition and make this selected transition dominant over all other competing processes.

Control over forbidden transitions can be used to make emitters which can preferably decay via multipolar or spin-forbidden transitions, allowing fine tuning of the radiation pattern and reshaping of the radiative interactions between different emitters. This control can also create emitters which prefer to emit multiple entangled photons simultaneously, rather than a single photon, which can lead to new sources of single photons and also entangled photons. Moreover, a single emitter can be configured to emit radiation with a tunable frequency and tunable angular spectrum.

Selective enhancement of forbidden transitions can be achieved by disposing emitters into surface phonon-polaritons (SPhPs) created near the surface of polar dielectrics. Polar dielectrics, such as hexagonal boron nitride (hBN) and silicon carbide (SiC), can confine electromagnetic energy in small volumes (e.g., on length scales potentially as short as 5 nm) via SPhPs, in a manner similar to plasmons in 2D materials. Unlike 2D plasmons, the SPhPs of polar dielectrics usually have extremely strong confinement (e.g., comparable to/higher than graphene) over a relatively narrow spectral band (e.g., a few THz). Moreover, these phonon polaritons can have substantially lower losses compared to plasmons.

The narrow bandwidth of phonon polaritons can be used to access forbidden transitions with high efficiency. In general, apparatus and methods described above can be configured to increase control over forbidden transitions by replacing the thin conductive layer with a thin polar dielectric layer. In addition, the plasmon fields near the surface of the thin conductive layer are replaced by phonon-polariton fields near the surface of the polar dielectric layer.

Figure 13:
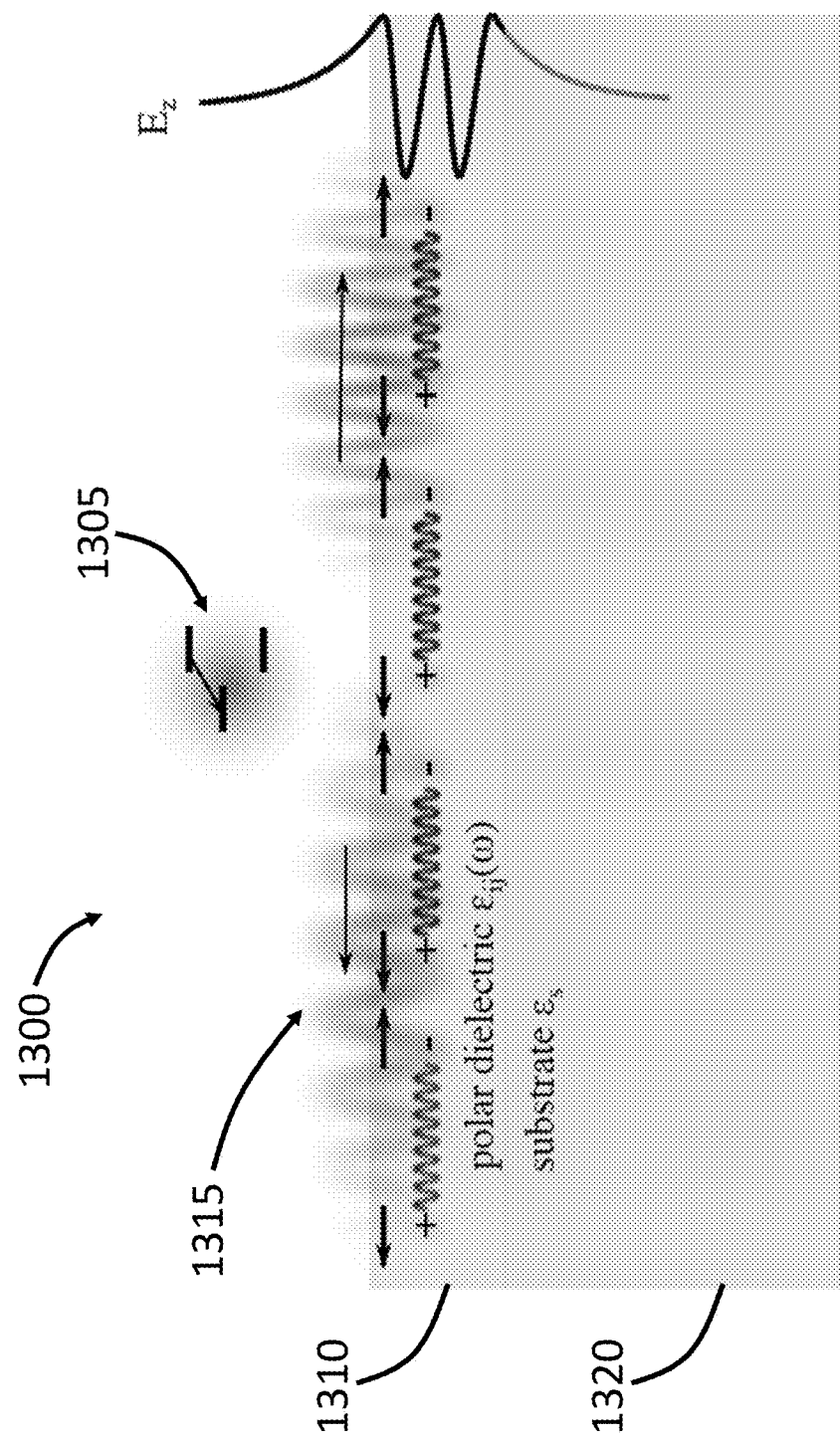
FIG. 13 shows a schematic of a system to turn an otherwise forbidden transition into a dominant transition using phonon-polaritons near the surface of a polar dielectric material.

FIG. 13 shows a schematic of a system 1300 to create dominant transitions that are otherwise forbidden in the absence of phonon-polariton fields. The system 1300 includes a polar dielectric layer 1310 disposed on a substrate 1320 to generate a phonon-polariton field 1315. The phonon-polariton field 1315 can be generated by any of the means discussed above to generate plasmon fields. An emitter 1305 is disposed near the surface of the polar dielectric layer 1310. The polar dielectric layer 1310 can include, for example, hBN or SiC. The thickness of the polar dielectric layer 1310 can be about 1 nm to about 20 nm (e.g., about 1 nm, about 2 nm, about 5 nm, about 10 nm, about 15 nm, or about 20 nm, including any values and sub ranges in between).

Polar dielectrics are a class of materials that support phonon-polariton modes in a narrow band of frequencies (called the Reststrahlen (or RS) band). These modes can be extremely highly confined (e.g., on scale of a few nanometers) at frequencies in the mid-IR region. With such extreme confinement comes great enhancement of forbidden transitions (e.g., multipolar, spin-flip phosphorescence, and multiphonon-polariton spontaneous emission). The enhanced forbidden process can be observable and can even be tens or hundreds of times faster than any competing one-photon process. Applications of these enhanced forbidden transitions include spectroscopy, sensing, quenching, broadband light-generation, and entangled-light generation. All apparatus and methods described above can be configured to use phonon-polaritons (instead of plasmons) by replacing the conductive layers with polar dielectric layers.

In free-space, an emitter given a choice between different transition pathways generally take the single-photon E1 (dipole) transition over other choices. However, in the presence of strongly confined modes over a narrow frequency band as shown in FIG. 13, the single-photon E1 transition can be negligibly enhanced while a forbidden transition is strongly enhanced (e.g., over 10 orders of magnitude relative to the enhancement of the competing E1 transition). As a result, this otherwise forbidden transition is strongly preferred and can be made dominant.

The mechanism of making an otherwise forbidden transition dominant can be illustrated via computing the rates of various forbidden transitions for emitters placed near films supporting SPhP modes. The calculated rates can be compared with the rates of nearby non-degenerate transitions (because in general atoms, states with different orbital angular momenta are non-degenerate).

It can be useful to make two observations before calculating the transition rates. First, there usually exist plenty of atoms that have conventionally forbidden transitions within the Reststrahlen band. In contrast, conventionally allowed transitions of these atoms are not within the Reststrahlen band. As used herein, the Reststrahlen band of a medium refers to an energy band, in which electromagnetic radiation does not propagate within the medium due to a change in refractive index concurrent with the specific absorbance band of the medium. For example, in lithium atoms, there is a quadrupolar d→s transition at 795 cm$^{-1}$. All other transitions fall outside of the Reststrahlen bands. There is also a d→s transition at 1611 cm$^{-1}$, which can potentially occur via emission of a pair of SPhPs. Again, all other competing transitions fall outside of the Reststrahlen bands.

Second, in emitters, such quantum dots or quantum wells, the energy levels can be tuned. As a result, many more possibilities arise for engineering conventionally forbidden transitions to fall within the Reststrahlen band of one or more SPhP supporting material.

To capture multipolar emission and multiphoton emission in the same formalism, fully quantum calculations can be carried out. The calculations here take losses into account rigorously through the formalism of macroscopic QED which is used to describe SPhPs. Light-matter interaction can be characterized by an interaction Hamiltonian:

$$H_{int} = \frac{e}{2m}(p \cdot A + A \cdot p) + \frac{e^2}{2m}A^2 \quad (1)$$

where the vector potential operator, A, in the presence of losses is given by:

$$A_i(r) = \sqrt{\frac{\hbar}{\pi\epsilon_0}} \int dr' \int d\omega' \frac{\omega'}{c^2} \sum_{k'} \sqrt{\text{Im}\epsilon(r', \omega')} \left(G_{ik'}(r, r', \omega')\hat{f}_{k'}(r', \omega') + H.c\right) \quad (2)$$

with $G_{ik}(r, r', \omega')$ being the dyadic Green function of the Maxwell equations for the material system presented in FIG. 13.

For the low losses characteristic of phonon-polaritons (and even often plasmon-polaritons), decay rates can be obtained with reasonable accuracy by neglecting the losses and writing the field operators in the form of an expansion over plane-wave phonon-polariton modes (more details are in Sections below). The vector potential in the lossless limit takes the form:

$$A = \sum_q \sqrt{\frac{\hbar}{2\epsilon_0 \omega_q}} (a_q F_q + H.c) \quad (3)$$

The modes $F_q$ satisfy:

$$\nabla \times \nabla \times F_q = \epsilon(\omega)\frac{\omega^2}{c^2} F_q,$$

and are normalized such that $$\frac{\hbar\omega}{2\epsilon_0} = \int dr F_q^* \cdot \frac{1}{2\omega}\frac{d(\epsilon\omega^2)}{d\omega} \cdot F_q.$$

In the vicinity of the emitter, the SPhP modes can be written as (after neglecting retardation): $F = F_0 e^{iq \cdot \rho - qz}\hat{e}(\hat{q})$, where $F_0$ is the field amplitude and $$\hat{e}(\hat{q}) = \frac{1}{\sqrt{2}}(\cos\theta, \sin\theta, i)$$

in Cartesian coordinates. The normalization can be proven rigorously to be consistent with dyadic Green function formalism. In the limit where there is no dissipation, these two expressions for the vector potential operator can generate equivalent decay rates, as can be shown by writing the Green function in the limit of no losses. The advantages of the Green function expression include the generality and the ability to characterize the impact of losses on decay rates. The advantages of the lossless formalism include the emphasis of the fact that the emission is into modes. Based on this, information of the angular spectrum of emitted phonon-polaritons can be more readily extracted. Both approached are used in the analysis here.

In multi-photon calculations where the dipole approximation is appropriate, a more convenient choice of interaction Hamiltonian can be given by $H_{int}=-d \cdot E+self\text{-}energy$. The self-energy term usually does not include creation or annihilation operators and thus can be irrelevant to the calculations here. In addition, it can be assumed that the phonon-polariton supporting materials can be well described by a local model (i.e., the dielectric constant of the phonon-polariton supporting materials is only frequency dependent). Agreement with a local model can be seen in hBN films as thin as 1 nm.

Creating Preferentially Non-Dipolar Emitter via Phonon-Polaritons

Via phonon-polaritons, an electron can be forced to decay via a multipolar single photon transition, even for multipolarities as high as 32-pole. A hydrogen atom is used here for illustration, but the general principle for creating high-efficiency access to forbidden transitions is independent of whether or not the atom in question is hydrogenic. As a result, the analysis presented here can be applied to a wide array of atoms, molecules, and artificial atoms, such as quantum dots, quantum wells, and quantum wires, among others. For example, the analysis here can be readily applied in accessing conventionally slow transitions in quantum dots, which have mesoscopic dimensions that allows control of forbidden transitions with significantly less polaritonic confinement.

Figures 14A, 14B, 14C:
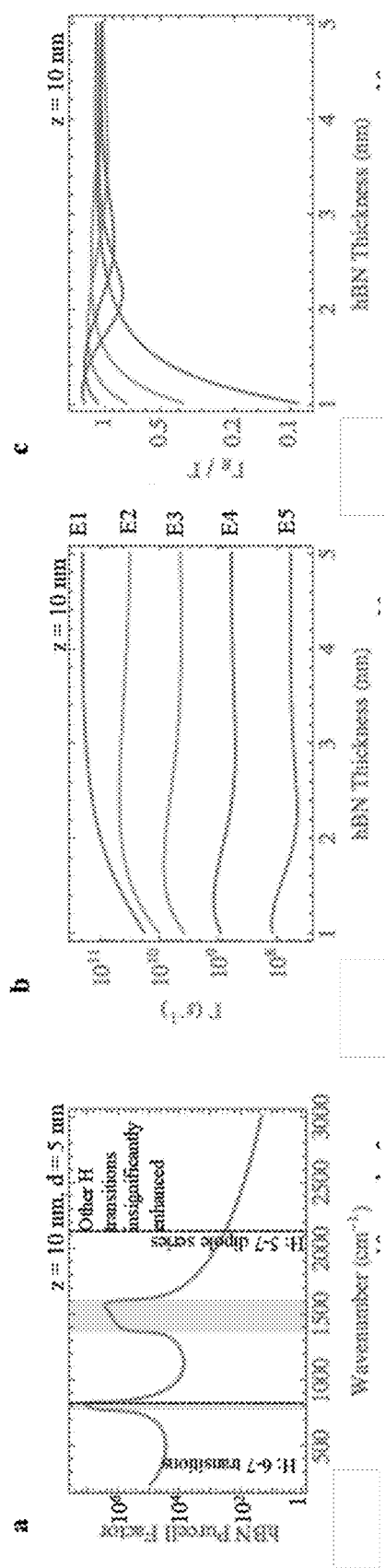

FIGS. 14A-14F show calculation results comparing the potential of phonon-polariton materials to force an electron to preferentially decay via multipolar transitions in hBN (hyperbolic) and SiC (nonhyperbolic). FIGS. 14A and 14D show calculated Purcell factors for a z-polarized dipole 10 nm away from an hBN layer and a SiC layer, respectively. The hBN and SiC layers have a thickness of about 5 nm. FIGS. 14B and 14E show calculated decay rates for multipolar transitions E1-E5 for an emitter (e.g., hydrogen) placed 10 nm away from the surface of hBN and SiC, respectively. FIGS. 14C and 14F show calculated radiative ratios FR/F of multipolar transitions in hBN and SiC, respectively, for the transitions considered in FIGS. 14B and 14E. The permittivity of the substrate is taken to be 11 for the case of hBN and 1.5 for the case of SiC. The damping constant for both materials is taken to be 5 cm$^{-1}$.

In calculations of FIGS. 14A-14F, the optic axis of hBN is along the direction that the thickness is measured (z-direction). The series of hydrogenic transitions 7{p, d, f g, h}(m=0)→6 s at 12.4 μm for 4H—SiC (isotropic) and hBN (hyperbolic) are considered. These transitions are respectively E1 (dipole), E2 (quadrupole), E3 (octupole), E4 (hexadecupole), and E5 (32-pole). FIGS. 14A and 14D plot the p-polarized Purcell spectra for a dipole emitter oriented in the z-direction (perpendicular to 5 nm thick hBN or 5 nm thick SiC), 10 nm above hBN/SiC in order to estimate the rates of competing dipole transitions. The Purcell spectra have a large peak in the Reststrahlen (RS) bands (highlighted as vertical bands in FIGS. 14A and 14D) but are nonzero outside of the RS bands mostly due to losses. For both hBN and SiC, the fastest nondegenerate transition (for reasons discussed above) in competition with a 7-6 transition is the 7-5 E1 transition with a lifetime of roughly 1 μs, which has been enhanced roughly an order of magnitude by losses.

FIG. 14B plots the transition rates of E1-E5 7-6 transitions for hydrogen above hBN as a function of hBN thickness. For small thicknesses of around 5 nm, even the E5 transition is faster than the 7-5 E1 transition. The 7-6 transition in hydrogen also coincides with the RS band of SiC. However, at the transition frequency (around 806 cm$^{-1}$), for a thickness of 5 nm, the very high-order multipolar transitions are quite slow and that these decays mostly occur as a result of the losses. The reason can be that the transition frequency is too close to the lower edge of the SiC RS band, meaning that the confinement of the mode at that frequency is not very high. A hypothetical emitter can be considered with a transition frequency of 920 cm$^{-1}$ but with the exact same multipole moments as those associated with the aforementioned Hydrogenic 7-6 transitions. In this case, the rates of high-order multipole transitions become extremely high (see FIG. 14E).

It can be informative to have some measure of which part of the decay comes from coupling to propagating modes. Even though phonon-polaritons have relatively low loss, the effects of losses can be amplified by bringing an emitter sufficiently close to a surface which is dissipative. For convenience, a quantity referred to as the radiative ratio, $r=\Gamma_R/\Gamma$ can be defined as the ratio of the decay rate computed assuming no losses ($\Gamma_R$) to the decay rate computed with losses taken into account ($\Gamma$). The radiative ratio can be a measure of the extent to which quenching dominates the decay dynamics insofar as a low r value suggests strong loss-dominated decay. The effect of losses can add new decay channels and modify (e.g., reduce) the density of states of radiative channels, as is known in the conventional Purcell effect with optical resonators. Therefore, the radiative ratio r can be greater than 1.

FIGS. 14C and 14F plot the r-values of the multipolar decays shown in FIGS. 14B and 14E for hBN and SiC, respectively, as a function of hBN and SiC thicknesses ranging from 1 to 5 nm. There exist regimes where the radiative ratio is around 1 for the different multipolar transitions, although the behavior at larger thicknesses for hyperbolic hBN versus isotropic SiC is noticeably different. For hBN, the radiative ratio stabilizes to about 1. For SiC, the efficiency keeps decreasing as the multipolar order increases.

The difference of the radiative ratio as a function of thickness shown in FIGS. 14C and 14F may be attributed to different hyperbolicity between hBN and SiC. The decay rate of an En transition can be proportional to $\int dq q^{2n} e^{-2qz_0}$ $Imr_p(q, \omega)$, where $r_p(q, \omega)$ is the p-polarized reflectivity of the air-polar dielectric-substrate system at the transition frequency, q is the wave vector, $z_0$ is the emitter-surface separation, and n is the multipolar order of the pure multipole emitter (n=1 for dipole, n=2 for quadrupole, etc.). This integral can be split into two parts—a pole contribution centered at the value of q satisfying the dispersion relation and a broad background which peaks around $1/z_0$. The broad background can vanish in the absence of dissipation and can often be qualitatively understood as the part of the decay rate coming from losses. Losses can dominate when $1/z_0 \gg q$. In hyperbolic systems like hBN, high-order modes can exist at q near $1/z_0$, meaning that losses do not dominate. On the other hand, in non-hyperbolic systems with thickness on the order of $1/z_0$, there can be no modes and generally losses can dominate. This effect can be especially pronounced for higher order multipole transitions because their rates depend much more sharply on wave vector.

Figures 15D, 15E, 15F:
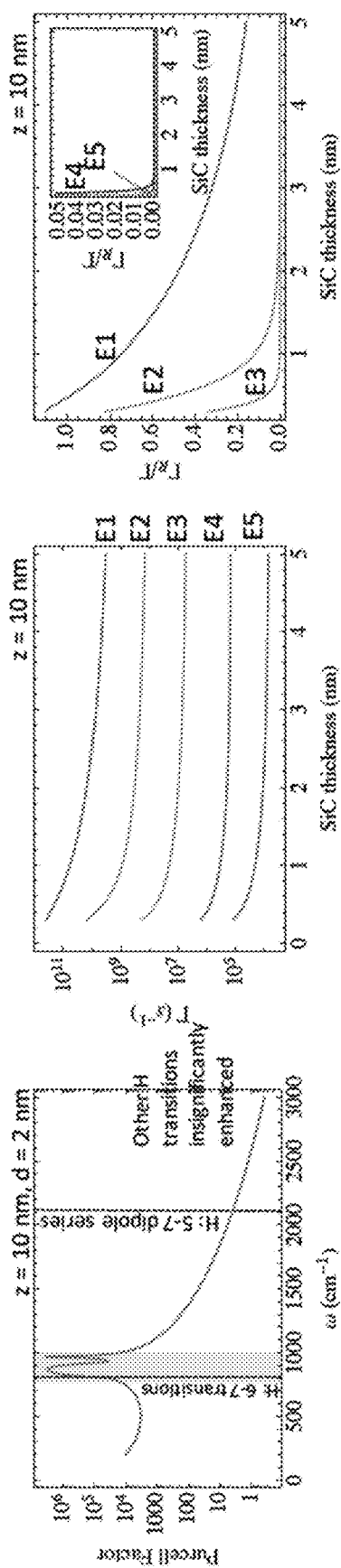

FIGS. 15A-15F show calculation results of multipolar transitions using parameters substantially similar to those used for FIGS. 14A-14F, except that the thickness of the polar dielectric layer (i.e., the hBN and SiC layers) is 2 nm. FIGS. 15A and 15D show calculated Purcell factors for a z-polarized dipole 10 nm away from hBN and SiC, respectively. FIGS. 15B and 15E show calculated decay rates for multipolar transitions E1-E5 for an emitter 10 nm away from the surface of hBN and SiC, respectively. FIGS. 15E and 15F show radiative efficiencies $\Gamma_R/\Gamma$ of multipolar transitions in hBN and SiC, respectively, for an emitter 10 nm away from the surface.

Emitting Entangled Photon Pairs with Tunable Frequency and Angular Spectrum

Phonon-polaritons can also be used to cause an electron to have two-photon spontaneous emission as its dominant transition, leading to a natural source of entangled photons. Moreover, this preferential emission of entangled photons can have a tunable angular and frequency spectrum. The emission spectra can be tuned through operating parameters, such as atom-surface separation, substrate index, and emitter frequency. Moreover, the emission spectra depend on the detailed electronic structure of the orbitals participating in the transition, allowing for a new degree of freedom by which to control two-polariton emitters.

A preferential emission of entangled photon pairs can occur with strong confinement ($\lambda_0/\lambda_{SPhP}$>100) over a narrow band, where $\lambda_0$ is the free space wavelength and $\lambda_{SPhP}$ is the wavelength of the phonon-polariton field. Under this condition, there is no SPhP mode at the frequency of competing one-photon transitions, such that electrons do not directly relax to the ground state via any competing one-photon transitions. At the same time, there can be SPhP modes at roughly half of the frequency of the transition in question (i.e., from excited state to ground state). In this case, the emission of a pair of polaritons, each of which is at approximately half of the frequency of the transition in question, can be enhanced by these SPhP modes.

The degree of confinement for an emitter to preferentially emit entangled photon pairs can depend, among others, the size of the emitter. In general, the free-space two-photon emission rates scale as four powers of the characteristic emitter length. Therefore, larger emitters, such as mesoscopic emitters and solid-state emitters, can have much larger free-space rates of two-photon emission. As a result, less enhancement of the free-space two-photon emission via phonon-polaritons can be used to achieve dominance of two-photon emission.

FIGS. 16A-16D show calculation results of a hydrogenic system considering an electron transition between 5 s and 4 s states via two-polariton spontaneous emission into cBN (cubic boron nitride) phonon polaritons. FIG. 16A shows Purcell spectra for a z-polarized dipole above 10 nm thick cBN at atom-surface separations of 5 nm, 10 nm, and 25 nm. FIGS. 16B-16D show two-photon Purcell spectra for an s→s transition as a function of photon frequency $\omega$ for atom-surface separations of 5 nm, 10 nm, and 25 nm, respectively. In each of FIGS. 16B-16D, the top curve denotes the Purcell spectra with losses accounted for and the bottom curve denotes the Purcell spectra for cBN with 100 times weaker losses. In each of FIGS. 16B-16D, both the overall two-photon transition rate between the 5 s and 4 s states of hydrogen and the corresponding radiative ratio ($\Gamma_R/\Gamma$) are estimated. The permittivity of the substrate is taken to be 2 and the damping constant for cBN is taken to be 5 cm$^{-1}$.

The one-photon transition frequency between the 5 s and 4 s state is about 2468 cm$^{-1}$ and the RS band of cBN is between about 1052 cm$^{-1}$ and about 1303 cm$^{-1}$. FIG. 16A shows the Purcell spectra for a first-order dipole transition for atom-surface separations of 5 nm, 10 nm, and 25 nm to get an order of magnitude estimate for the rates of the competing dipole transitions at first order. At 5 nm, the fastest competing transition occurs with a lifetime on the order about 100 ns. At 10 nm and 25 nm, the order of magnitude of the competing E1 transition is closer to 1 µs. FIGS. 16B-16D show the spectrum of two-photon emission from 5 s-4 s (due to cBN phonon-polaritons), in addition to the lifetime of the two-photon transition and the r-values (as defined in the previous section).

For an s→s transition, the spectral enhancement factor, defined as the ratio of the SPhP emission spectra, $d\Gamma/d\omega$, to the free-space emission spectrum $d\Gamma_0/d\omega$, can be given by:

$$\text{Spectral Enhancement} = \frac{\frac{d\Gamma}{d\omega}}{\frac{d\Gamma_0}{d\omega}} = \frac{1}{2}F_p(\omega)F_p(\omega_0 - \omega) \quad (4)$$

where $F_p(\omega)$ is the Purcell factor for a dipole perpendicular to the surface and is related to the imaginary part of the reflectivity of the air-polar dielectric-substrate system by $$F_p(\omega) = \frac{3}{2k_0^2}\int dq q^2 e^{-2qz_0} \text{Im} r_p(q, \omega),$$

where $k_0$ is the free-space photon wave vector.

FIGS. 16B-16D show that the lifetimes of two-photon spontaneous emission for an emitter 5 nm, 10 nm, or 25 nm away from the surface of 10 nm thick cBN is 1.7 ns, 68 ns, or 28 µs, respectively. The r-values are 0.51, 1.02, or 1.12, respectively. Thus, two-photon spontaneous emission into phonon-polaritons can be nearly two orders of magnitude faster than single-photon dipole transitions. This is in sharp contrast to the situation in free-space, where two-photon spontaneous emission is roughly 8-10 orders of magnitude slower. Therefore, using phonon-polaritons can create a source of a pair of entangled polaritons with very high efficiency.

Figures 17A, 17B, 17C:
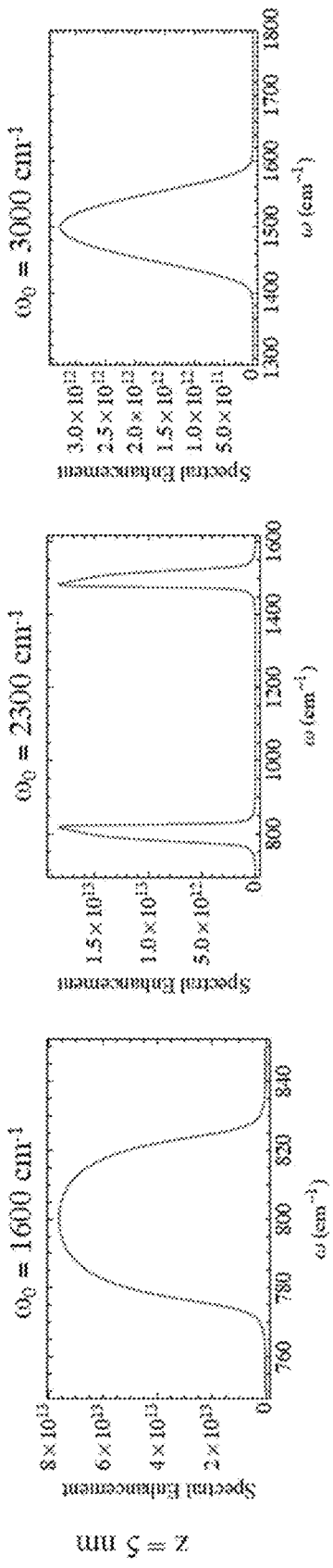
Figures 17G, 17H, 17I:
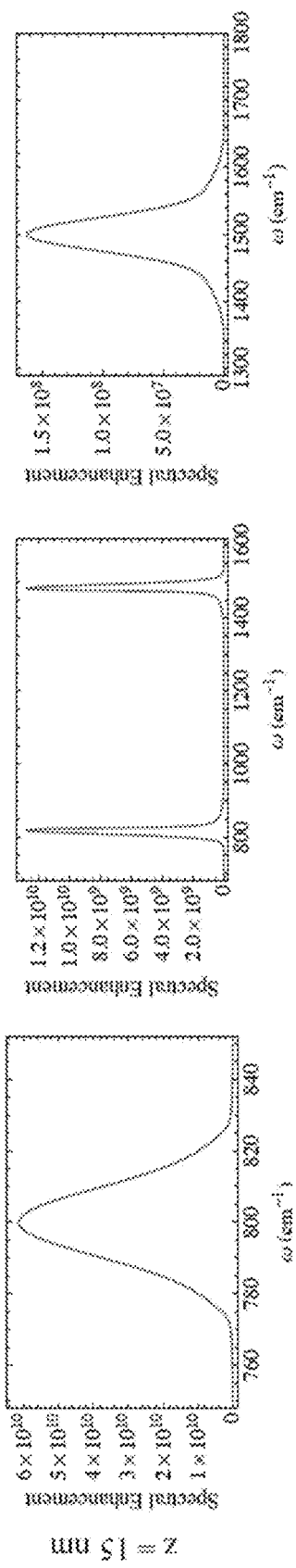

FIGS. 17A-17I show two-polariton Purcell spectral enhancement (defined as in Equation (4)) for a spherical emitter as a function of emitter frequency at different distances away from an hBN surface. FIGS. 17A-17C show the spectral enhancement with the emitter placed 5 nm away from the hBN surface. FIGS. 17D-17F show the spectral enhancement with the emitter placed 10 nm away from the hBN surface. FIGS. 17G-17I show the spectral enhancement with the emitter placed 15 nm away from the hBN surface. The spectral enhancement is defined as a function of emitter frequency ($\omega_0$=1600, 2300, 3000 cm$^{-1}$) and emitter-surface separation ($z_0$=5 nm, 10 nm, 15 nm). Instead of cBN, hBN is used in calculating the results in FIGS. 17A-17I to show that two-photon spectral enhancements are achievable in other materials (the spectral enhancement is of the same order of magnitude as that in cBN) and also to show a large number of frequency bands where a two-photon emitter can be created.

FIGS. 17A-17I show that hBN offers very high spectral enhancement in three different frequency bands, as opposed to one in isotropic polar dielectrics, allowing for compatibility with many more electronic systems. This can be attributed to inter-combination, which is a two-photon emission through near-field polaritons that can occur via two photons in the lower RS band, two photons in the upper RS band, or one in the upper RS band and one in the lower RS band. A material having three separate RS bands can offer six frequency ranges for two-photon emission. In addition, increasing the emitter separation can decrease the intensity of the emission spectrum, as well as the width of the emission spectrum (e.g., by about a factor of 2 when the separation goes from 5 nm to 15 nm). This allows flexible tuning of not only the emission rate but also the emission spectrum with atom-surface separation.

FIGS. 18A-18D show plots of the angular spectra of two-photon emission with the initial state at s, $d_{xy}$, $d_{xz}$, and $d_{yz}$, respectively. As discussed in more details below, the angle and frequency spectrum of two-photon emission, $S(\omega, \theta, \theta')$ can be proportional to:

$$S(\omega, \theta, \theta') \sim \left| \sum_{ij} \hat{e}_i^*(\theta) \hat{e}_j^*(\theta') T_{ij}(\omega) \right|^2 \quad (5)$$

$$T_{ij}(\omega) = $$

$$T_{ji}(\omega_0 - \omega) \sim \sum_n \left( \frac{d_i^{gn} d_j^{ne}}{E_e - E_n - \hbar\omega} + \frac{d_j^{gn} d_i^{ne}}{E_e - E_n - \hbar(\omega_0 - \omega)} \right)$$

where $d^{ab}$ denotes a dipole matrix element between states a and b, n denotes an intermediate atomic state, g denotes the ground state, e denotes the excited state, and $E_i$ is the energy of the ith state. The $\hat{e}_i(\theta)$ are the phonon-polariton polarizations in the vicinity of the emitter, given by $1/\sqrt{2}(\cos(\theta), \sin(\theta), i)$.

The angular dependence of the spectrum in Equation (5) can lead to very different angular spectra for different transitions. Table 1 below shows the angular spectrum as a function of different transitions (at $\omega=\omega_0/2$). Strictly speaking, the angular spectrum is frequency dependent. However, due to the narrowness of the RS band(s), this narrowing due to frequency change can be neglected, and only the spectrum at half the transition frequency is used. Remarkably, just by changing the initial state of the system, one can change whether the entangled pairs are preferentially emitted in the same direction (illustrated in FIGS. 18B and 18C) or in opposite directions (illustrated in FIG. 18A).

FIGS. 16A-18D show that using highly confined, narrow-band phonon-polaritons can cause an electron to preferentially decay via the emission of a pair of entangled photons. Moreover, it is possible to do this at many frequency ranges in the mid IR, especially in anisotropic materials such as hBN, due to their multiple Reststrahlen bands. The frequency spectrum of such a source of entangled near-field photons can be reshaped by emitter frequency and emitter-surface separation. Furthermore, coherent effects arising from electronic structure can provide a significant degree of freedom to tune the angular shape of the radiation. For some initial and final orbital configurations, the entangled pairs are emitted in the same direction, while in other configurations, the entangled pairs are emitted in opposite directions. There are a number of ways to populate a particular initial state. One is by exciting the atoms with light of a fixed polarization. Another way is to simply excite the atoms with the appropriate frequency, appropriate in systems with less extreme degeneracy than hydrogen.

TABLE 1

Angular spectrum of two-photon radiation versus initial electronic states

| Transition | Angular Spectrum |
| --- | --- |
| s → s | $\sin^4\left(\frac{\theta - \theta'}{2}\right)$ |
| $d_{xy}$ → s | $\sin^2(\theta + \theta')$ |
| $d_{xz}$ → s | $(\cos\theta + \cos\theta')^2$ |
| $d_{yz}$ → s | $(\sin\theta + \sin\theta')^2$ |

FIGS. 13-18D together show that the combination of extremely high confinement factors and a narrow (but with a finite width) spectral range can be employed to construct atomic emitters that are fundamentally different than any existing emitter. For example, phonon-polaritons can be employed to make emitters which preferentially emit via multipolar transitions, allowing reshaping of the radiation of emitters and the radiative interaction between different emitters. This effect can occur in both hBN and thin polar dielectrics. Hyperbolicity in hBN can also enhance the emission.

In another example, using this general technique of extremely high confinement over a narrow spectral range can make emitters which preferentially decay via the emission of entangled pairs of near-field photons, even when single-photon dipole transitions are allowed. This can be realized over many frequency ranges in the mid-IR and the frequency spectra can be relatively broad and tunable. Coherent quantum effects can also reshape the angular spectrum of emission of these entangled pairs, thereby allowing shaped electron wave packets to reshape the spectrum of entangled photon radiation.

As nearly all atoms have electronic transitions in the mid-IR, techniques discussed above can be applied to a large portion of the periodic table. Vibrational transitions may also be used to observe these effects. Moving beyond the mid-IR to the near-IR, these techniques can realize the effects using "shaped polaritonic media" (e.g., nano-resonators of graphene or plasmonic crystals of graphene and other 2D plasmonic materials) supporting (respectively) narrow spectral response or photonic bandgaps. Applications of these techniques include, but are not limited to: spectroscopy for inferring electronic transitions that are otherwise not amenable to probing with photons, sensors based on forbidden transitions, quantum radiation sources (e.g., on-demand generation of single photons and entangled pairs of photons), new platforms for quantum non-linear optics, nonlinearities at the single photon level, turning narrow-band emitters into broadband emitters, turning narrow-band absorbers into broadband absorbers, and in general the ability to completely reshape the ostensibly fixed optical properties of materials.

Theoretical Analysis of Emitter-Phonon-Polariton Coupling

The coupling of atomic emitters with the phonon-polaritons characteristic of polar crystals, such as hBN and SiC, can be carried out by considering atom-field interactions governed by the non-relativistic Pauli-Schrodinger Hamiltonian H:

$$H = H_a + H_{em} + H_{int} \quad (6)$$

$$H_a = \left(\sum_i \frac{p_i^2}{2m_e} - \frac{e^2}{4\pi\epsilon_0 r_i}\right)$$

$$H_{em} = \sum_k \int dr \int d\omega \hbar\omega \left(f_k^\dagger(r,\omega)f_k(r,\omega) + \frac{1}{2}\right)$$

$$H_{int} = \sum_i \frac{e}{2m}(p_i \cdot A(r_i) + A(r_i) \cdot p_i) + \frac{e^2}{2m}A^2(r_i)$$

where $H_a$ is the atomic Hamiltonian, $H_{int}$ is the atom-field interaction, A is the vector potential operator, and B is the magnetic field operator. The minimal-coupling interaction Hamiltonian presented above is related to the more well-known dipole interaction Hamiltonian: $-d\cdot E$+self-energy, by a unitary transformation in the long-wavelength (dipole) approximation.

The analysis can take losses fully into account via the formalism of macroscopic quantum electrodynamics (QED). One physical difference between QED with losses and QED without losses lies in the elementary excitations. In the lossless formalism, the excitations can be seen as quanta of electromagnetic modes. In the lossy formalism, the excitations may not be seen as quanta of electromagnetic modes because the modes are typically not well-defined. Instead, the elementary excitations are dipoles which are induced in the material. These excitations can be characterized by their position, frequency, and orientation.

The vector potential operator in the framework of macroscopic QED can be given by:

$$A_i(r) = \sqrt{\frac{\hbar}{\pi\epsilon_0}} \quad (7)$$

$$\int d\omega' \sum_j \frac{\omega'}{c^2} \int dr' \sqrt{\mathrm{Im}\epsilon(r',\omega')} \, G_{ij}(r,r';\omega') \hat{f}_j(r',\omega') + H.c.$$

where $G_{ij}$ is the dyadic Green function of the Maxwell equations:

$$\nabla \times \nabla \times G_i - \varepsilon(r,\omega)\frac{\omega^2}{c^2}G_i = \delta(r-r')\hat{e}_i. \quad \hat{f}_j^{(+)}(r,\omega)$$

annihilates (or creates) a lossy excitation at frequency $\omega$, at position r, and in direction j, and satisfies bosonic commutation relations, namely: $[\hat{f}_i(r,\omega), \hat{f}_j^+(r',\omega')] = \delta_{ij}\delta(\omega-\omega')\delta(r-r')$. When applying the Fermi Golden Rule, the initial state is $|e, 0\rangle$, while the final states are of the form $|g, x_1\omega_1 k_1, \ldots x_N\omega_N k_N\rangle$, where g represents a ground atomic state, e represents an excited atomic state, and $|x\omega k\rangle = \hat{f}_k^+(x,\omega)|0\rangle$ represents an excitation of the electromagnetic field.

As prescribed by Equation (7), the Green function of a phonon-polariton supporting system can be solved. One solution can use the approximation that the wave vector of the phonon polaritons emitted is usually much larger than the photon wavelength $\omega/c$. This is the electrostatic limit, in which the electric field is approximately longitudinal, i.e. $E = -\nabla\phi$, where $\phi$ satisfies the Laplace equation: $\partial_i \varepsilon_{ij}(\omega) \partial_j \phi = 0$.

The Green function for the potential $G_\phi(r, r', \omega)$ can be defined by: $\partial_i \varepsilon_{ij}(\omega) \partial_j G_\phi(r, r', \omega) = 0$ and can be related to the Green function for the electric field by: $G_{ij}^E(r, r', \omega)$, by:

$$G_{ij}^E(r,r',\omega) = -\frac{c^2}{\omega^2} \partial_i \partial_j' G^\phi(r,r',\omega).$$

The Green function can then be solved for both an anisotropic polar crystal and an isotropic polar crystal with the same methods.

Expressing the Green function for the potential as $$\frac{1}{2\pi}\int dq\, c(q,z) e^{iq\cdot\rho}:$$

$$r_p = \frac{e^{2qd}(\epsilon-1)(\epsilon_s+\epsilon) + (\epsilon+1)(\epsilon_s-\epsilon)}{e^{2qd}(\epsilon+1)(\epsilon_s+\epsilon) + (\epsilon-1)(\epsilon_s-\epsilon)} \quad (8)$$

In the case of an isotropic polar dielectric and $$r_p = \frac{(\sqrt{r}\epsilon_\parallel + i)(\epsilon_s + i\sqrt{r}\epsilon_\parallel)e^{2iq\sqrt{r}d} + (\sqrt{r}\epsilon_\parallel - i)(\epsilon_s - i\sqrt{r}\epsilon_\parallel)}{(\sqrt{r}\epsilon_\parallel - i)(\epsilon_s + i\sqrt{r}\epsilon_\parallel)e^{2iq\sqrt{r}d} + (\sqrt{r}\epsilon_\parallel + i)(\epsilon_s - i\sqrt{r}\epsilon_\parallel)} \quad (9)$$

in the case of a hyperbolic polar dielectric in the RS bands where r is the absolute value of the anisotropy ratio, defined by $r = |\epsilon_\perp/\epsilon_\parallel|$. The location of the poles of the imaginary part of the reflectivity in $(\omega, q)$ space gives the dispersion relation $\omega(q)$. When losses are present, the imaginary part $\mathrm{Im}(r_p)$ is centered around the dispersion relation.

Although all of the decay rates can be computed through this Green function formalism, it may be difficult from this formalism to extract information such as the angular spectrum of emitted polaritons. The reason for this is that concepts like the angular spectrum assume emission into well-defined modes with some propagation direction. But when losses are present, modes may be ill-defined. Therefore, a different formalism is used to capture the emission into propagating phonon polaritons and thus to derive the angular spectrum of entangled photons.

In lossless dielectrics, the vector potential can be expressed in the form of a mode expansion:

$$A = \sum_n \sqrt{\frac{\hbar}{2\epsilon_0 \omega_n}} (F_n a_n + hc) \quad (10)$$

where $F_n$ are the orthonormal modes of the Maxwell equations, normalized such that $\int dr |F|^2 = 1$. It can be shown that by taking the Green function formalism in the lossless limit, a mode expansion for the field operators in terms of eigenmodes (of the form above) can be derived for polaritons, where the second quantization operators for the modes satisfy canonical commutation relations provided that the field modes are normalized such that:

$$\frac{1}{2\omega}\int dr F^*(r) \cdot \frac{d(\epsilon_r \omega^2)}{d\omega} \cdot F(r) = \frac{\hbar\omega}{2\epsilon_0}. \quad (11)$$

In the electrostatic limit $qc/\omega \gg 1$, the fields in the vicinity of a well-localized emitter above a polar dielectric can have the form: $F \sim e^{iq\cdot\rho - qz}\hat{e}(\hat{q})$, where $$\hat{e}(\hat{q}) = \frac{\hat{q} + i\hat{z}}{\sqrt{2}}.$$

$\hat{q}$ can be expressed as $\cos\theta\hat{x} + \sin\theta\hat{y}$. This fact can be used to compute the angular spectrum of pairs of emitted phonon-polaritons in sections below.

It can be shown that the decay rate for a transition of any multipolar order including losses is given by:

$$\Gamma = \frac{2e^2}{\hbar\epsilon_0 m_e^2 \omega_0^2} \frac{1}{(2\pi)^2} \int dq q |\langle g|(\hat{e}(q)\cdot p)e^{iq\cdot\rho-qz}|e\rangle|^2 \text{Im} r_p \quad (12)$$

where $r_p$ is the p-polarized complex reflectivity of the air-polar dielectric-substrate system.

The calculations for multipolar transition rates are for the case in which the initial and final wave functions have their z-projected angular momentum to be zero (i.e., $m_i = m_f = 0$). In this case, the angular integral is simply $2\pi$, and q can be set to be in a particular direction, called x. It is usually the case that in the matrix element in Equation (10) there is one main contributing term from the series expansion of the exponential. That is to say:

$$|\langle e|e^{ik(-ix-(x-x0))}\hat{e}_0 * \cdot \nabla|g\rangle|^2 = C_n q^{2(n-1)} \quad (13)$$

where n=1 for dipole (E1) transitions, n=2 for quadrupole (E2) transitions, and so on, meaning that the decay rates can be given by:

$$\Gamma = \frac{e^2}{\pi\hbar\epsilon_0 m_e^2 \omega_0^2} C_q \int dq q^{2n} e^{-2qz_0} \text{Im} r_p(q, \omega_0) \quad (14)$$

The frequency spectra of spontaneous emission of N excitations of the lossy electromagnetic field can be derived by considering special cases N=2. The results fully incorporate losses and elucidate the contribution of quenching and intercombination of quenching and polariton launching to the decay of an excited emitter. The derivation proceeds by application of the Fermi Golden rule at N-th order in perturbation theory as applied to transitions between an initial state the initial state is $|i_N, 0\rangle$, while the final states are of the form $|i_0, x_1\omega_1 k_1, \ldots x_N\omega_N k_N\rangle$.

The Fermi Golden rule for this process can be expressed as:

$$\Gamma = \frac{2\pi}{\hbar^2 N!} \prod_{i=1}^{N} \left( \int dx_i \int d\omega_i \sum_{k_i} \right) \quad (15)$$

$$\left| \sum_{i_1 \ldots i_{N-1}} V_{i_N, i_{N-1}} \prod_{k=1}^{N-1} \frac{V_{i_k, i_{k-1}}}{E_{i_0} - E_{i_k}} \right|^2 \delta\left(\omega_0 - \sum_{i=1}^{N} \omega_i\right)$$

where $i_0$ denotes an initial electronic state and $i_N$ denotes a final electronic state. For simplicity, the perturbation operator V can be taken as the dipole operator $-d\cdot E$. An interesting quantity is the spectrum of radiation, which provides information about the probability of emitting an entangled N-tuple of polaritons at frequencies ($\omega_1; \omega_2; \ldots \omega_N$). Since one of the polariton frequencies can be fixed by energy conservation, Equation (15) becomes:

$$\frac{d\Gamma}{d\omega_1 \ldots d\omega_{N-1}} = \quad (16)$$

$$\frac{2\pi}{\hbar^2 N!} \prod_{i=1}^{N} \left( \int dx_i \sum_{k_i} \right) \left| \sum_{i_1 \ldots i_{N-1}} V_{i_N, i_{N-1}} \prod_{k=1}^{N-1} \frac{V_{i_k, i_{k-1}}}{E_{i_0} - E_{i_k}} \right|^2$$

where it is understood that $\omega_N = \omega_0 - \Sigma_{i=1}^{N-1} \omega_i$.

The sum over intermediate states $i_1, i_2, \ldots i_{N-1}$ can include both electronic and electromagnetic degrees of freedom. Denoting the atomic degrees of freedom as $n_i$, for a fixed set of electronic intermediate states $\{n_1, n_2, \ldots n_{N-1}\}$, there are N! terms corresponding to the different orderings of the intermediate excitations of the electromagnetic field. This can be used for simplification because it means that the same electromagnetic terms can appear in each term of the sum, even when the electronic degrees of freedom are varied. As a result, the same electromagnetic terms can be factored out. This simplification in turn allows connecting the spectrum of N-excitation emission processes to the Purcell factor of a dipole at each frequency by which a photon is emitted.

To proceed, three identities can be defined:

$$V_{i_j, i_{j-1}} = \langle n_j, x_j\omega_j k_j, x_{j-1}\omega_{j-1} k_{j-1}, \ldots, \quad (17)$$

$$x_1\omega_1 k_1 | d_i E_i | n_{j-1}, x_{j-1}\omega_{j-1} k_{j-1}, \ldots, x_1\omega_1 k_1 \rangle$$

$$= i\sqrt{\frac{\hbar}{\pi\epsilon_0}} d_{ij}^{n_j, n_{j-1}} \frac{\omega_j^2}{c^2} \sqrt{\text{Im}\epsilon(x_j), \omega_j} G_{i_j k_j}^*(r_0, x_j, \omega_j),$$

$$\frac{\omega^2}{c^2} \int dr \text{Im}\epsilon(r, \omega)(GG^\dagger)(r_0, r, \omega) = \text{Im} G(r_0, r_0, \omega)$$

For a dipole polarized in the z-direction and a material which is uniform in the xy-plane:

$$\text{Im} G_{ij}(r_0, r_0, \omega) = \frac{\omega}{3\pi c} F_p(r_0, r_0, \omega) D_{ij}, \quad (18)$$

where $D = \text{diag}(\frac{1}{2}, \frac{1}{2}, 1)$ and $F_p$ is the Purcell factor for one-photon emission for the z-polarized dipole (frequency $\omega$ and position $r_0$) near this material.

Defining the sum over permutations and intermediate states as $T_{i1, i2, \ldots iN}$, and $E = \hbar\omega_0 y$, and using the three facts above derives:

$$\frac{d\Gamma}{dy_1 \ldots dy_{N-1}} = \frac{2\pi\omega_0}{N!}\left(\frac{2}{3\pi}\right)^N \alpha^N k_0^{2N} \left[\sum_{i=1}^{N} y_i^3 F_p(y_i)\right] \quad (19)$$

$$\sum_{i_1 \ldots i_N} D_{i_1 i_1} \ldots D_{i_n i_n} |T_{i_1 \ldots i_N}(y_1 \ldots y_N)|^2$$

Equation (19) indicates that the enhancement of the spectrum at some set of frequencies is proportional to the enhancement of emission at each of those frequencies. For example, in the special case where two lossy excitations are emitted, equation (19) becomes:

$$\frac{d\Gamma}{dy} = \pi\omega_0 \left(\frac{2}{3\pi}\right)^2 \alpha^2 k_0^4 y^3 (1-y)^3 F_p(y) F_p(1-y) \sum_{ij} D_{ii} D_{jj} |T_{ij}|^2 \qquad (20)$$

The analysis can focus on the case in which the transition is between two s states. In that case, only the xx, yy, and zz terms are relevant of $T_{ij}$, indicating that the above sum over i and j becomes $3/2 T_{zz}$, making emission rate for two lossy excitations:

$$\frac{d\Gamma}{dy} = \frac{2}{3\pi}\omega_0 \alpha^2 k_0^4 y^3 (1-y)^3 F_p(y) F_p(1-y) |T_{zz}|^2 \qquad (21)$$

Using the fact that the free-space differential decay rate is given by:

$$\frac{4}{3\pi}\alpha^2 k^4 y^3 (1-y)^3 |T_{zz}|^2 \qquad (22)$$

it follows that the spectral enhancement (defined in the main text) is:

$$\frac{\frac{d\Gamma}{d\omega}}{\frac{d\Gamma_0}{d\omega}} = \frac{1}{2} F_p(\omega) F_p(\omega_0 - \omega) \qquad (23)$$

The expression for the two lossy excitation differential decay rate derived by taking the N=2 case of our N-photon emission formula is consistent with one that we derived in the specific context of two-plasmon spontaneous emission for 2D plasmons.

The angular spectrum of radiation of phonon-polaritons emitted by an excited atomic electron can then be computed via the quantity:

$$S(\omega, \theta, \theta') \equiv \frac{d\Gamma}{d\omega d\theta d\theta'} \qquad (24)$$

For simplification, the analysis can focus on excitation of propagating polaritons and not loss-excitations. In this case, the pole contribution can be extracted from the imaginary part of the p-polarized reflectivity. This is equivalent to writing field operators in the lossless limit. Writing the second-order Fermi Golden Rule for the transition rate between an initial state $|e, 0\rangle$ and the continuum of final states $|g, qq'\rangle$ can derive:

$$\frac{d\Gamma}{d\omega d\theta d\theta'} = \qquad (25)$$

$$\frac{1}{16\pi^3 \hbar^2} \frac{q(\omega) q(\omega_0 - \omega)}{v_g(\omega) v_g(\omega_0 - \omega)} \left| \sum_{ij} \frac{\langle g, qq' | d \cdot E | i_1 \rangle \langle i_1 | d \cdot E | e, 0\rangle}{E_i - E_{i_1} + i0^+} \right|^2$$

where $v_g$ is the group velocity $d\omega/dq$. Inserting the definition of the operators, the spectrum is given by:

$$S(\omega, \theta, \theta') = \frac{\alpha^2 c^2}{4\pi} \omega(\omega_0 - \omega) \frac{q(\omega) q(\omega_0 - \omega)}{v_g(\omega) v_g(\omega_0 - \omega)} |F_q^{*i} F_{q'}^{*j} T_{ij}|^2 \qquad (26)$$

where:

$$T_{ij}(\omega) = \sum_n \frac{x_j^{gn} x_i^{ne}}{\omega_i - \omega_n - \omega} + \frac{x_i^{gn} x_j^{ne}}{\omega_i - \omega_n - (\omega_0 - \omega)} = T_{ji}(\omega_0 - \omega), \qquad (27)$$

Equations (25) and (26) can then be used to extract the form of the angular spectrum of entangled photons as a function of the electronic orbitals participating in the transition. To illustrate the degree of control over the angular spectrum of emitted photon pairs, four cases are considered here. In all four cases, the final states are s states. But the initial states of the four cases are: s, $d_{xy}$, $d_{yz}$, and $d_{xz}$, respectively.

In the case where the initial state is an s state, $T_{ij}=0$ and $i\neq j$. This is because of the dipole approximation, which fixes the intermediate state to be a p state. Therefore, if $i\neq j$, then $T_{ij}$ has a sum of terms like $\langle s|x_i|p_k\rangle\langle p_k|x_j|s\rangle$, where $p_k=p_x$, $p_y$, $p_z$. Each of these terms individually vanishes, and the entire tensor can vanish as well. Moreover, $T_{xx}=T_{yy}=T_{zz}=T$ because $\langle p_x|x|s\rangle=\langle p_y|y|s\rangle=\langle p_z|z|s\rangle$. Therefore:

$$S(\omega, \theta, \theta') = \qquad (28)$$
$$|T|^2 (\cos\theta\cos\theta' + \sin\theta\sin\theta' - 1)^2 = 4|T|^2 \sin^4\left(\frac{\theta-\theta'}{2}\right). (s\to s)$$

In the case where the initial state is $d_{xy}$, the only contributing terms are $T_{xy}$ and $T_{yx}$. This is because the $d_{xy}$ has an angular dependence that can be written in Cartesian coordinates as xy. This claim can be proved by examining the $T_{zi}$ components. If one of the indices is z, then it can either be the case that the intermediate state is a $p_z$ state (to have overlap with the s state), or that there is a matrix element of the form $\langle p_i|z|d_{xy}\rangle$. The first case gives zero because $d_{xy}$ has no transition dipole moment with z. The second case also gives zero because $d_{xy}$ has no z-polarized dipole moment with any p orbital. Thus the $T_{zi}$ components vanish. The $T_{xx}$ and $T_{yy}$ components also vanish because $d_{xy}$ has no (x,y)-polarized dipole moment with $p_{x,y}$. Therefore:

$$S(\omega,\theta,\theta')=(T_{xy}(\omega)\cos\theta\sin\theta'+T_{xy}(\omega_0-\omega)\sin\theta\cos\theta')^2 \cdot (d_{xy}\to s) \qquad (29)$$

A nearly identical argument to the one above (replace all y's with z's or all x's with z's) can be used to derive results when initial states are $d_{xz}$ and $d_{yz}$:

$$S(\omega,\theta,\theta')=(T_{xz}(\omega)\cos\theta+T_{xz}(\omega_0-\omega)\cos\theta')^2 \cdot (d_{xz}\to s)$$

$$S(\omega,\theta,\theta')=(T_{yz}(\omega)\sin\theta+T_{yz}(\omega_0-\omega)\sin\theta')^2 \cdot (d_{yz}\to s) \qquad (30)$$

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus comprising:
   a conductive layer having a thickness less than 10 nm;
   a radiation source, in radiative communication with the conductive layer, to emit an excitation beam into the conductive layer, the excitation beam generating a two-dimensional (2D) plasmon field near a surface of the conductive layer;
   a light source, in optical communication with the conductive layer, to illuminate a sample in the 2D plasmon field with a probe beam, the sample absorbing at least one spectral component of the probe beam; and
   a detector, in optical communication with the light source, to detect absorption of the at least one spectral component by the sample,
   wherein the sample absorbs at least a portion of the 2D plasmon field via a transition forbidden in an absence of the 2D plasmon field.

2. The apparatus of claim 1, wherein the conductive layer comprises a 2D conductor.

3. The apparatus of claim 1, wherein the conductive layer comprises graphene.

4. The apparatus of claim 1, wherein the conductive layer comprises at least one of silver, gold, or $DySi_2$, and the apparatus further comprises a substrate, disposed below the conductive layer, to support the conductive layer, the substrate comprising at least one of Si, $Si_3N_4$, or $SiO_2$.

5. The apparatus of claim 1, wherein the radiation source comprises an optical radiation source and the excitation beam comprises a light beam.

6. The apparatus of claim 5, wherein the conductive layer comprises a grating.

7. The apparatus of claim 6, wherein the grating has a period of about 5 nm to about 20 nm.

8. The apparatus of claim 5, further comprising:
a conductive tip, disposed at a distance less than 30 nm away from the surface of the conductive layer, to generate the 2D plasmon field.

9. The apparatus of claim 1, further comprising:
a spacer layer, disposed on the conductive layer, to hold the sample, the spacer layer having a thickness less than 10 nm.

10. The apparatus of claim 1, wherein the sample comprises a gaseous sample, the apparatus further comprising:
a chamber to receive the gaseous sample.

11. A method comprising:
generating a two-dimensional (2D) plasmon field near a surface of a conductive layer having a thickness less than 5 nm;
disposing a sample within the 2D plasmon field, the sample absorbing at least a portion of the 2D plasmon field via a transition forbidden in an absence of the 2D plasmon field;
illuminating the 2D plasmon field with a probe beam, the sample absorbing at least one spectral component in the probe beam; and
detecting the absorption of the at least one spectral component.

12. The method of claim 11, wherein generating the 2D plasmon field comprises coupling a light beam into the conductive layer via a grating fabricated in the conductive layer, the grating having a period of about 5 nm to about 20 nm.

13. The method of claim 11, wherein generating the 2D plasmon field comprises irradiating a conductive tip, disposed at a distance less than 10 nm away from the surface of the conductive layer, to excite the 2D plasmon field.

14. The method of claim 11, wherein disposing the sample into the 2D plasmon field comprises disposing the sample onto a spacer layer disposed on the conductive layer, the spacer layer having a thickness less than 10 nm.

15. The method of claim 11, wherein disposing the sample into the 2D plasmon field comprises flowing the sample in a gaseous state to a chamber containing the conductive layer.

* * * * *